US009358395B2

(12) United States Patent  
Tweden et al.

(10) Patent No.: US 9,358,395 B2  
(45) Date of Patent: *Jun. 7, 2016

(54) NEURAL MODULATION DEVICES AND METHODS

(71) Applicant: EnteroMedics Inc., St. Paul, MN (US)

(72) Inventors: Katherine S. Tweden, Mahtomedi, MN (US); Jonathan J. Waataja, Plymouth, MN (US); Adrianus P. Donders, Andover, MN (US); Mark B. Knudson, Shoreview, MN (US)

(73) Assignee: EnteroMedics Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/453,183

(22) Filed: Aug. 6, 2014

(65) Prior Publication Data

US 2014/0350632 A1 Nov. 27, 2014

Related U.S. Application Data

(62) Division of application No. 13/154,846, filed on Jun. 7, 2011, now Pat. No. 8,825,164.

(60) Provisional application No. 61/353,850, filed on Jun. 11, 2010.

(51) Int. Cl.
*A61N 1/36* (2006.01)
*A61N 1/05* (2006.01)
(Continued)

(52) U.S. Cl.
CPC ........ *A61N 1/36178* (2013.01); *A61N 1/36007* (2013.01); *A61N 1/36053* (2013.01);
(Continued)

(58) Field of Classification Search
CPC . A61N 1/36; A61N 1/36007; A61N 1/36053; A61N 1/63082; A61N 1/36085
USPC ....................................... 607/2, 40, 116, 133
See application file for complete search history.

(56) References Cited

U.S. PATENT DOCUMENTS

| 3,128,760 A | 4/1964 | Baker |
| 3,411,507 A | 11/1968 | Wingrove |

(Continued)

FOREIGN PATENT DOCUMENTS

| EP | 1 666 087 A1 | 2/1998 |
| EP | 0 865 800 A2 | 9/1998 |

(Continued)

OTHER PUBLICATIONS

"Bravo™ pH Monitoring System Catheter-Free pH Testing", document No. UC 200300235 EN N15344, Medtronic, Inc., Minneapolis, Minnesota, USA (2002).

(Continued)

*Primary Examiner* — Christopher A Flory
(74) *Attorney, Agent, or Firm* — Merchant & Gould P.C.

(57) ABSTRACT

A system for designing a therapy or for treating a gastrointestinal disorder or a condition associated with excess weight in a subject comprising at least one electrode configured to be implanted within a body of the patient and placed at a vagus nerve, the electrode also configured to apply therapy to the vagus nerve upon application of a therapy cycle to the electrode; an implantable neuroregulator for placement in the body of the patient beneath the skin layer, the implantable neuroregulator being configured to generate a therapy cycle, wherein the therapy cycle comprises an on time during which an electrical signal is delivered, the electrical signal comprising: a) a set of pulses applied at a first selected frequency of about 150-10,000 Hz, wherein each pulse of the set of pulses has a pulse width of at least 0.01 milliseconds and less than the period of the first selected frequency.

10 Claims, 8 Drawing Sheets

(51) Int. Cl.
    *A61N 1/372*           (2006.01)
    *A61N 1/378*           (2006.01)

(52) U.S. Cl.
    CPC ........ *A61N1/36085* (2013.01); *A61N 1/36117* (2013.01); *A61N 1/0509* (2013.01); *A61N 1/3787* (2013.01); *A61N 1/37235* (2013.01)

(56) References Cited

U.S. PATENT DOCUMENTS

| | | | |
|---|---|---|---|
| 4,114,625 A | 9/1978 | Onat | |
| 4,198,963 A | 4/1980 | Barkalow et al. | |
| 4,541,432 A | 9/1985 | Molina-Negro et al. | |
| 4,702,254 A | 10/1987 | Zabara | |
| 4,776,349 A | 10/1988 | Nashef et al. | |
| 4,867,164 A | 9/1989 | Zabara | |
| 4,979,511 A | 12/1990 | Terry et al. | |
| 5,025,807 A | 6/1991 | Zabara | |
| 5,188,104 A | 2/1993 | Wernicke et al. | |
| 5,199,430 A | 4/1993 | Fang et al. | |
| 5,215,086 A | 6/1993 | Terry, Jr. et al. | |
| 5,215,089 A | 6/1993 | Baker, Jr. et al. | |
| 5,226,429 A | 7/1993 | Kuzmak | |
| 5,231,988 A | 8/1993 | Wernicke et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,292,344 A | 3/1994 | Douglas | |
| 5,299,569 A | 4/1994 | Wernicke et al. | |
| 5,330,515 A | 7/1994 | Rutecki et al. | |
| 5,335,657 A | 8/1994 | Terry et al. | |
| 5,344,438 A | 9/1994 | Testerman | |
| 5,370,675 A | 12/1994 | Edwards et al. | |
| 5,423,872 A | 6/1995 | Cigaina | |
| 5,437,291 A | 8/1995 | Pasricha et al. | |
| 5,514,175 A | 5/1996 | Kim et al. | |
| 5,531,778 A | 7/1996 | Maschino et al. | |
| 5,540,730 A | 7/1996 | Terry, Jr. et al. | |
| 5,571,150 A | 11/1996 | Wernicke et al. | |
| 5,601,604 A | 2/1997 | Vincent | |
| 5,620,955 A | 4/1997 | Knight et al. | |
| 5,690,691 A | 11/1997 | Chen et al. | |
| 5,707,400 A | 1/1998 | Terry, Jr. et al. | |
| 5,716,385 A | 2/1998 | Mittal et al. | |
| 5,747,060 A | 5/1998 | Sackler et al. | |
| 5,749,907 A | 5/1998 | Mann | |
| 5,830,434 A | 11/1998 | Taylor et al. | |
| 5,836,994 A | 11/1998 | Bourgeois | |
| 5,861,014 A | 1/1999 | Familoni | |
| 5,919,216 A | 7/1999 | Houben et al. | |
| 5,967,977 A | 10/1999 | Mullis et al. | |
| 5,995,872 A | 11/1999 | Bourgeois | |
| 6,002,964 A | 12/1999 | Feler et al. | |
| 6,083,249 A | 7/2000 | Familoni | |
| 6,091,992 A | 7/2000 | Bourgeois et al. | |
| 6,093,167 A | 7/2000 | Houben et al. | |
| 6,097,984 A | 8/2000 | Douglas | |
| 6,098,629 A | 8/2000 | Johnson et al. | |
| 6,104,955 A | 8/2000 | Bourgeois | |
| 6,111,715 A | 8/2000 | Tsuchiya et al. | |
| 6,129,726 A | 10/2000 | Edwards | |
| 6,135,978 A | 10/2000 | Houben et al. | |
| 6,148,222 A | 11/2000 | Ramsey, III | |
| 6,216,039 B1 | 4/2001 | Bourgeois | |
| 6,238,423 B1 | 5/2001 | Bardy | |
| 6,243,607 B1 | 6/2001 | Mintchev et al. | |
| 6,261,280 B1 | 7/2001 | Houben et al. | |
| 6,261,572 B1 | 7/2001 | Donovan | |
| 6,290,961 B1 | 9/2001 | Aoki et al. | |
| 6,292,703 B1 | 9/2001 | Meier et al. | |
| 6,308,105 B1 | 10/2001 | Duysens et al. | |
| 6,312,708 B1 | 11/2001 | Donovan | |
| 6,341,236 B1 | 1/2002 | Osorio et al. | |
| 6,364,899 B1 | 4/2002 | Dobak, III | |
| 6,369,079 B1 | 4/2002 | Rubin et al. | |
| 6,405,732 B1 | 6/2002 | Edwards et al. | |
| 6,418,346 B1 | 7/2002 | Nelson et al. | |
| 6,449,511 B1 | 9/2002 | Mintchev et al. | |
| 6,473,644 B1 | 10/2002 | Terry, Jr. et al. | |
| 6,532,388 B1 | 3/2003 | Hill et al. | |
| 6,558,708 B1 | 5/2003 | Lin | |
| 6,571,127 B1 | 5/2003 | Ben-Haim et al. | |
| 6,587,719 B1 | 7/2003 | Barrett et al. | |
| 6,587,725 B1 | 7/2003 | Durand et al. | |
| 6,591,137 B1 | 7/2003 | Fischell | |
| 6,600,956 B2 | 7/2003 | Maschino et al. | |
| 6,609,025 B2 | 8/2003 | Barrett et al. | |
| 6,610,713 B2 | 8/2003 | Tracey | |
| 6,611,715 B1 | 8/2003 | Boveja | |
| 6,612,983 B1 | 9/2003 | Marchal | |
| 6,622,038 B2 | 9/2003 | Barrett et al. | |
| 6,684,105 B2 | 1/2004 | Cohen et al. | |
| 6,746,474 B2 | 6/2004 | Saadat | |
| 6,760,626 B1 | 7/2004 | Boveja | |
| 6,826,428 B1 | 11/2004 | Chen et al. | |
| 6,832,114 B1 | 12/2004 | Whitehurst et al. | |
| 6,853,862 B1 | 2/2005 | Marchal et al. | |
| 6,879,859 B1 | 4/2005 | Boveja | |
| 6,895,278 B1 | 5/2005 | Gordon | |
| 6,901,295 B2 | 5/2005 | Sharma | |
| 6,928,320 B2 | 8/2005 | King | |
| 6,993,391 B2 | 1/2006 | Flesler et al. | |
| 7,054,690 B2 | 5/2006 | Imran | |
| 7,072,720 B2 | 7/2006 | Puskas | |
| 7,076,307 B2 | 7/2006 | Boveja et al. | |
| 7,142,910 B2 | 11/2006 | Puskas | |
| 7,167,750 B2 | 1/2007 | Knudson et al. | |
| 7,292,890 B2 | 11/2007 | Whitehurst et al. | |
| 7,299,091 B2 | 11/2007 | Barrett et al. | |
| 7,310,557 B2 | 12/2007 | Maschino et al. | |
| 7,340,306 B2 | 3/2008 | Barrett | |
| 7,343,201 B2 | 3/2008 | Mintchev | |
| 7,346,398 B2 | 3/2008 | Gross et al. | |
| 7,389,145 B2 | 6/2008 | Kilgore et al. | |
| 7,444,183 B2 | 10/2008 | Knudson et al. | |
| 7,444,184 B2 | 10/2008 | Boveja | |
| 7,489,969 B2 | 2/2009 | Knudson et al. | |
| 7,613,515 B2 | 11/2009 | Knudson et al. | |
| 7,620,454 B2 | 11/2009 | Dinsmoor et al. | |
| 7,620,455 B2 | 11/2009 | Maschino | |
| 7,630,769 B2 | 12/2009 | Knudson | |
| 7,672,727 B2 | 3/2010 | Donders et al. | |
| 7,693,577 B2 | 4/2010 | Knudson | |
| 7,706,875 B2 | 4/2010 | Buras et al. | |
| 7,720,539 B2 | 5/2010 | Mintchev | |
| 7,720,540 B2 | 5/2010 | Knudson et al. | |
| 7,729,771 B2 | 6/2010 | Knudson | |
| 7,734,355 B2 | 6/2010 | Cohen et al. | |
| 7,738,961 B2 | 6/2010 | Sharma | |
| 7,742,818 B2 | 6/2010 | Dinsmoor et al. | |
| 7,822,486 B2 | 10/2010 | Foster et al. | |
| 7,833,279 B2 | 11/2010 | Knudson et al. | |
| 7,844,338 B2 | 11/2010 | Knudson et al. | |
| 7,917,226 B2 | 3/2011 | Nghiem et al. | |
| 7,937,145 B2 * | 5/2011 | Dobak | A61B 5/4872 607/2 |
| 7,962,214 B2 | 6/2011 | Byerman et al. | |
| 7,986,995 B2 | 7/2011 | Knudson et al. | |
| 8,010,204 B2 | 8/2011 | Knudson et al. | |
| 8,239,027 B2 | 8/2012 | Imran | |
| 8,260,426 B2 | 9/2012 | Armstrong et al. | |
| 8,538,533 B2 * | 9/2013 | Knudson | A61N 1/05 607/40 |
| 8,712,529 B2 * | 4/2014 | Sharma et al. | 607/40 |
| 2001/0012828 A1 | 8/2001 | Aoki et al. | |
| 2001/0051787 A1 | 12/2001 | Haller et al. | |
| 2002/0016617 A1 | 2/2002 | Oldham | |
| 2002/0032468 A1 | 3/2002 | Hill et al. | |
| 2002/0052336 A1 | 5/2002 | Yerxa et al. | |
| 2002/0055779 A1 | 5/2002 | Andrews | |
| 2002/0072780 A1 | 6/2002 | Foley | |
| 2002/0087192 A1 | 7/2002 | Barrett et al. | |
| 2002/0094962 A1 | 7/2002 | Ashley et al. | |
| 2002/0103424 A1 | 8/2002 | Swoyer et al. | |

(56) References Cited

U.S. PATENT DOCUMENTS

| | | |
|---|---|---|
| 2002/0161360 A1 | 10/2002 | Carroll |
| 2002/0198570 A1 | 12/2002 | Puskas |
| 2002/0198571 A1 | 12/2002 | Puskas |
| 2003/0014086 A1 | 1/2003 | Sharma |
| 2003/0018367 A1 | 1/2003 | DiLorenzo |
| 2003/0040785 A1 | 2/2003 | Maschino et al. |
| 2003/0045909 A1 | 3/2003 | Gross et al. |
| 2003/0045914 A1 | 3/2003 | Cohen et al. |
| 2003/0074039 A1 | 4/2003 | Puskas |
| 2003/0135245 A1 | 7/2003 | Campos |
| 2003/0135248 A1 | 7/2003 | Stypulkowski |
| 2003/0144708 A1 | 7/2003 | Starkebaum |
| 2003/0144709 A1 | 7/2003 | Zabara et al. |
| 2003/0171789 A1 | 9/2003 | Malek et al. |
| 2003/0181958 A1 | 9/2003 | Dobak, III |
| 2003/0181959 A1 | 9/2003 | Dobak, III |
| 2003/0195601 A1 | 10/2003 | Hung et al. |
| 2003/0212440 A1 | 11/2003 | Boveja |
| 2004/0015201 A1 | 1/2004 | Greenstein |
| 2004/0039425 A1 | 2/2004 | Greenwood-Van Meerveld |
| 2004/0039427 A1 | 2/2004 | Barrett et al. |
| 2004/0059383 A1 | 3/2004 | Puskas |
| 2004/0086531 A1 | 5/2004 | Barron |
| 2004/0089313 A1 | 5/2004 | Utley et al. |
| 2004/0111126 A1 | 6/2004 | Tanagho et al. |
| 2004/0127953 A1 | 7/2004 | Kilgore et al. |
| 2004/0167583 A1 | 8/2004 | Knudson et al. |
| 2004/0172084 A1 | 9/2004 | Knudson et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0176812 A1 | 9/2004 | Knudson et al. |
| 2004/0181178 A1 | 9/2004 | Aldrich et al. |
| 2004/0193229 A1 | 9/2004 | Starkebaum et al. |
| 2004/0236381 A1 | 11/2004 | Dinsmoor et al. |
| 2004/0236382 A1 | 11/2004 | Dinsmoor et al. |
| 2004/0243182 A1 | 12/2004 | Cohen et al. |
| 2004/0249416 A1 | 12/2004 | Yun et al. |
| 2004/0254616 A1 | 12/2004 | Rossing et al. |
| 2005/0021101 A1 | 1/2005 | Chen et al. |
| 2005/0038484 A1 | 2/2005 | Knudson et al. |
| 2005/0049655 A1 | 3/2005 | Boveja et al. |
| 2005/0070970 A1 | 3/2005 | Knudson et al. |
| 2005/0070974 A1 | 3/2005 | Knudson et al. |
| 2005/0075693 A1 | 4/2005 | Toy et al. |
| 2005/0131485 A1 | 6/2005 | Knudson et al. |
| 2005/0137644 A1 | 6/2005 | Boveja et al. |
| 2005/0143378 A1 | 6/2005 | Yun et al. |
| 2005/0143412 A1 | 6/2005 | Puskas |
| 2005/0143787 A1 | 6/2005 | Boveja et al. |
| 2005/0149141 A1 | 7/2005 | Starkebaum |
| 2005/0149146 A1 | 7/2005 | Boveja et al. |
| 2005/0149148 A1 | 7/2005 | King |
| 2005/0192644 A1 | 9/2005 | Boveja et al. |
| 2005/0203501 A1 | 9/2005 | Aldrich et al. |
| 2005/0222638 A1* | 10/2005 | Foley ............ A61N 1/36007 607/40 |
| 2005/0240231 A1 | 10/2005 | Aldrich et al. |
| 2005/0267542 A1 | 12/2005 | David et al. |
| 2006/0015151 A1 | 1/2006 | Aldrich |
| 2006/0030919 A1 | 2/2006 | Mrva et al. |
| 2006/0036293 A1 | 2/2006 | Whitehurst et al. |
| 2006/0041277 A1 | 2/2006 | Deem |
| 2006/0100668 A1 | 5/2006 | Ben-david et al. |
| 2006/0149345 A1* | 7/2006 | Boggs, II ............ A61N 1/0556 607/118 |
| 2006/0161217 A1 | 7/2006 | Jaax et al. |
| 2006/0173507 A1* | 8/2006 | Mrva ............ A61N 1/0556 607/39 |
| 2006/0190053 A1 | 8/2006 | Dobak, III |
| 2006/0212089 A1 | 9/2006 | Tass et al. |
| 2006/0229685 A1 | 10/2006 | Knudson et al. |
| 2006/0247722 A1 | 11/2006 | Maschino et al. |
| 2006/0247737 A1 | 11/2006 | Olson |
| 2007/0027484 A1 | 2/2007 | Guzman et al. |
| 2007/0043400 A1 | 2/2007 | Donders et al. |
| 2007/0100377 A1 | 5/2007 | Armstrong et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0162084 A1 | 7/2007 | Chen et al. |
| 2007/0203521 A1 | 8/2007 | Dobak et al. |
| 2007/0233193 A1 | 10/2007 | Craig |
| 2007/0239226 A1 | 10/2007 | Overstreet |
| 2008/0021512 A1 | 1/2008 | Knudson et al. |
| 2008/0065158 A1* | 3/2008 | Ben-Ezra ............ A61N 1/36071 607/2 |
| 2008/0077174 A1 | 3/2008 | Mische |
| 2008/0086179 A1 | 4/2008 | Sharma |
| 2008/0147137 A1 | 6/2008 | Cohen et al. |
| 2008/0195171 A1 | 8/2008 | Sharma |
| 2008/0275514 A1 | 11/2008 | Ben-David et al. |
| 2008/0300654 A1 | 12/2008 | Lambert et al. |
| 2009/0118777 A1* | 5/2009 | Iki ............ A61N 1/36007 607/2 |
| 2009/0187230 A1 | 7/2009 | Dilorenzo |
| 2009/0210019 A1 | 8/2009 | Kim et al. |
| 2009/0228078 A1 | 9/2009 | Zhang et al. |
| 2009/0254143 A1 | 10/2009 | Tweden et al. |
| 2009/0306739 A1 | 12/2009 | DiLorenzo |
| 2010/0063563 A1* | 3/2010 | Craig ............ A61N 1/36082 607/45 |
| 2010/0094375 A1 | 4/2010 | Donders et al. |
| 2010/0241183 A1 | 9/2010 | DiLorenzo |
| 2010/0274308 A1* | 10/2010 | Scott ............ A61N 1/36135 607/9 |
| 2010/0292754 A1 | 11/2010 | Gliner |
| 2010/0298905 A1* | 11/2010 | Simon ............ A61N 1/3601 607/40 |
| 2011/0071589 A1 | 3/2011 | Starkebaum et al. |
| 2011/0130804 A1 | 6/2011 | Lin et al. |
| 2011/0137365 A1* | 6/2011 | Ben-Ezra ............ A61N 1/36071 607/17 |
| 2011/0295335 A1 | 12/2011 | Sharma et al. |
| 2011/0295336 A1 | 12/2011 | Sharma et al. |
| 2011/0307023 A1* | 12/2011 | Tweden ............ A61N 1/36007 607/3 |
| 2011/0307027 A1 | 12/2011 | Sharma et al. |
| 2011/0307028 A1 | 12/2011 | Sharma et al. |
| 2012/0022608 A1 | 1/2012 | Libbus et al. |
| 2012/0022617 A1 | 1/2012 | Tockman et al. |
| 2012/0053653 A1 | 3/2012 | Hiernaux et al. |
| 2012/0059431 A1 | 3/2012 | Williams et al. |
| 2012/0065698 A1 | 3/2012 | Errico et al. |
| 2012/0071946 A1 | 3/2012 | Errico et al. |
| 2012/0078319 A1 | 3/2012 | De Ridder |
| 2012/0083855 A1 | 4/2012 | Gross et al. |
| 2012/0101874 A1 | 4/2012 | Ben-Haim et al. |
| 2012/0136408 A1 | 5/2012 | Grill et al. |
| 2012/0232610 A1 | 9/2012 | Soffer et al. |
| 2012/0239108 A1 | 9/2012 | Foutz et al. |
| 2012/0253378 A1 | 10/2012 | Makower et al. |
| 2012/0259380 A1 | 10/2012 | Pyles |
| 2012/0259389 A1* | 10/2012 | Starkebaum ............ A61B 5/0006 607/62 |
| 2013/0035740 A1* | 2/2013 | Sharma et al. ............ 607/40 |

FOREIGN PATENT DOCUMENTS

| | | |
|---|---|---|
| EP | 0 896 828 A2 | 2/1999 |
| EP | 1 004 330 A1 | 5/2000 |
| WO | 01/41671 | 6/2001 |
| WO | 01/43821 | 6/2001 |
| WO | 02/26320 | 4/2002 |
| WO | 02/065896 | 8/2002 |
| WO | 2004/036377 | 4/2004 |
| WO | 2004/064918 | 8/2004 |
| WO | 2004/082763 | 9/2004 |
| WO | 2004/093981 | 11/2004 |
| WO | 2004/110551 | 12/2004 |
| WO | 2006/023498 | 3/2006 |
| WO | 2012/044472 | 4/2012 |

(56) References Cited

FOREIGN PATENT DOCUMENTS

| WO | 2012/060874 | 5/2012 |
|---|---|---|
| WO | 2013/008541 | 1/2013 |
| WO | 2014145239 A1 | 9/2014 |

OTHER PUBLICATIONS

"Medical Care for Obese Patients", U.S. Department of Health and Human Services, National Institute of Diabetes and Digestive and Kidney Diseases, pp. 1-6, NIH Publication No. 03-5335 (Feb. 2003).
"Obesity and Technology: Can the stomach be fooled", Reuters (Apr. 26, 2006), 3 pages, http://news.yahoo.com/s/nm/20060426/us_nm/bizfeature_obesity_technology_de&printer as printed on (May 23, 2006).
Accarino et al, "Attention and Distraction: Effects on Gut Perception", Gastroenterology, 113:415-422 (1997).
Accarino et al, "Gut Perception in Humans Is Modulated by Interacting Gut Stimuli", Am. J. Physiol. Gastrointestinal Liver Physiol., 282:G220-G225 (2002).
Accarino et al, "Modification of Small Bowel Mechanosensitivity by Intestinal Fat", Gut, 48:690-695 (2001).
Accarino et al, "Selective Dysfunction of Mechanosensitive Intestinal Afferents in Irritable Bowel Syndrome", Gastroenterology, 108:636-643 (1994).
Accarino et al, "Symptomatic Responses to Stimulation of Sensory Pathways in the Jejunum", Am. J. Physiol., 263:G673-G677 (1992).
Aggarwal et al., "Predominant Symptoms in Irritable Bowel Syndrome Correlate with Specific Autonomic Nervous System Abnormalities", Gastroenterol, 106:945-950 (1994).
Amaris et al., "Microprocessor controlled movement of solid colonic content using sequential neural electrical stimulation", Gut, 50:475-479 (2002).
Balaji et al., "A Safe and Noninvasice Test for Vagal Integrity Revisited", Archive Surgery, 137:954-959 (2002).
Balemba et al., "Innervation of the extrahepatic biliary tract", The Anatomical Record Part A: Discoveries in Molecular, Cellular, and Evolutionary Biology; 2004: vol. 280A, Issue 1, pp. 836-847.
Bard® Minnesota Four Lumen Esophagogastric Tamponade Tube for the Control of Bleeding from Esophageal Varices (Instructions for Use), C. R. Bard, Inc., Covington, GA, USA (1998).
Baron et al., "Acute Necrotizing Pancreatitis", New England J. of Medicine, 340(18):1412-1417 (1999).
Batterham et al., "Inhibition of Food Intake in Obese Subjects by Peptide YY3-36", New England J. Med., pp. 941-948 (Sep. 4, 2003).
Beglinger et al., "Postprandial Control of Gallbladder Contraction and Exocrine Pancreatic Secretion in Man", Euro. J. of Clinical Investigation, pp. 827-834 (1992).
Bell et al., "The Interplay Between Hydrogen Ions, Bicarbonate Ions and Osmolality in the Anterior Duodenum Modulating Gastric Function in the Conscious Calf", J. Physiol., pp. 331-341 (1981).
Benini "Gastric Emptying and Dyspeptic Symptoms in Patients with Gastroesophageal Reflux", Amer. J. of Gastroenterology, pp. 1351-1354 (1996).
Benini et al., "Omeprazole Causes Delay in Gastric Emptying of Digestible Meals", Digestive Diseases and Sciences, pp. 469-474 (1996).
Berthoud et al., "Characteristics of Gastric and Pancreatic Reponses to Vagal Stimulation with Varied Frequencies: Evidence for Different Fiber Calibers?", J. Auto. Nervous Sys., pp. 77-84 (1987).
Biron et al., "Clinical Experience with Biliopancreatic Bypass and Gastrectomy or Selective Vagotomy for Morbid Obesity", Canadian J. of Surg., 29(6):408-410 (1986).
Boss et al., Laparoscopic Truncal Vagotomy for Severe Obesity: Six Month Experience in 10 Patients from a Prospective, Two-Center Study, Proceedings of the 24th Annual Meeting, American Society for Metabolic & Bariatric Surgery, Plenary Session Abstracts, (Abstract No. 44) (Jun. 2007) (reprinted from http://www.asbs.org/archive/abstracts/plenary_edited_2007.pdf).
Bourde et al., "Vagal Stimulation: II. Its Effect on Pancreatic Secretion in Conscious Dogs", Annals of Surgery, pp. 357-364 (1970).

Brancatisano, R., et al., "Implantation Technique of a Novel Vagal Blockade Medical Device for the Treatment of Obesity," IFSO-APC OSSANZ Conference 2008: Mar. 25-28, 2009, Hilton Cairns, Queensland Conference Program Handbook.
Brancastisano et al., "Empower: A 12-Month Randomized, Prospective Clinical Trial: Safety and Effectiveness of VBLOC Therapy," 23rd Annual Scientific Conference of the Obesity Surgery Society of Australia and New Zealand, OSSANZ Conference 2010: The Changing Shape of Bariatrics, Nov. 10-12, Wednesday Nov. 10 10:30 am-12 noon, Tasmania Hotel Grand Chancellor, Hobart, Conference Program Handbook.
Burneo et al., "Weight Loss Associated With Vagus Nerve Stimulation", Neurology, 59:463-464 Aug. 1 of 2, 2002.
Camilleri et al., "Determinants of Response to a Prokinetic Agent in Neuropathic Chronic Intestinal Motility Disorder", American Gastroenterological Association, 106(4):916-923 (1994).
Camilleri et al., "Vagal Blocking for Obesity control (VBLOC): Plasma Pancreatic Polypeptide (PPP) Response to a Standardized Sham Meal Challenge," The Obesity Society 2007 Annual Scientific Meeting, Oct. 20-24, 2007, New Orleans Louisiana. Supplement to Obesity, vol. 15, Program Abstract Supplement, Sep. 2007.
Camilleri et al., "Intra-abdominal Vagal Blocking (VBLOC therapy): Clinical Results with a New Implantable Medical Device," Surgery, 143(6):723-731, Jun. 2008.
Camilleri et al., "Selection of Electrical Algorithms to Treat Obesity with Intermittent Vagal Block Using an Implantable Medical Device," Surgery for Obesity and Related Diseases, Official Journal of the American Society for Bariatric Surgery, 5(2):224-229, Mar./Apr. 2009.
Camillerl et al., "Vagal Blocking for Obesity Control (Vbloc): Plasma Pancreatic Polypeptide (PPP) Response to a Standardized Sham Meal Challenge," *Obesity*, 15(Supp, Abstract No. 20-OR):A6-A7 (Sep. 2007).
Cann et al., "Irritable Bowel Syndrome: Relationship of Disorders in the Transit of a Single Solid Meal to Symptoms Patterns", Gut, 24:405-411(1983).
Chang et al., "Long-Term Results of Duodenectomy with Highly Selective Vagotomy in the Treatment of complicated Duodenal Ulcers", Amer. J. of Surg., 181:372-376 (2001).
Chatzicostas et al., "Balthazar computed tomography severity index is superior to Ranson criteria and APACHE II and III scoring systems in predicting acute pancreatitis outcome", J. Clinical Gastroenterology, 36(3):253-260 (2003).
Chey et al., "Neural Hormonal Regulation of Exocrine Pancreatic Secretion", Pancreatology, pp. 320-335 (2001).
Chey, "Regulation of Pancreatic Exocrine Secretion", Int'l J. of Pancreatology, pp. 7-20 (1991).
Cigaina, "Gastric Pacing as Therapy for Morbid Obesity", Obesity Surgery, 12(Supp):12S-16S (2002).
Coffin et al, "Somatic Stimulation Reduces Perception of Gut Distention in Humans", Gastroenterology, 107:1636-1642 (1994).
Collins et al., "Reduces Calorie Intake and Weight Loss during Vagal Block (VBLOC Therapy) in Morbidly Obese Patients with Type 2 Diabetes Mellitus," 23rd Annual Scientific Conference of the Obesity Surgery Society of Australia and New Zealand, OSSANZ Conference 2010: The Changing Shape of Bariatrics, Nov. 10-12, Thursday Nov. 11 10:30 am-12 noon, Tasmania Hotel Grand Chancellor, Hobart, Conference Program Handbook.
Cuomo et al., "Functional Dyspepsia Symptoms, Gastric Emptying and Satiety Provocation Test: Analysis of Relationships", Scand J Gastroenterol, 36:1030-1036 (2001).
Cyberonics, Inc. 2001 Annual Report, pp. 1, 5-7 and 16 (2001).
Cyberonics, Inc. 2003 Form 10-K to Securities and Exchange Commission, pp. 1 and 10 as printed on May 23, 2006 from http://www.secinfo.com/dsvRu.23yb.htm.
D'Argent, "Gastric Electrical Stimulation: Preliminary Results", Obesity Surgery, 12(Supp):21S-25S (2002).
Dapoigny et al., "Vagal influence on colonic motor activity in conscious nonhuman primates", Am. J. Physiol., 262:G231-G236 (1992).
De Vault et al., "Updated Guidelines for the Diagnosis and Treatment of Gastroesophageal Reflux Disease", Am J Gastroenterol, 94:1434-1442 (1999).

(56) References Cited

OTHER PUBLICATIONS

Drossman, "Rome II: A Multinational Consensus Document on Gastrointestinal Disorders—The Functional Gastrointestinal Disorders and the Rome II Process", Gut, 45(Supp II):II1-II5 (1999).
Easton, "The Nerve Impulse Seen From Outside", Florida State University, Department of Biological Science, Jul. 2000 available on line at http://www.bio.fsu.edu/faculty-easton_actionpotential.htm (topics 1-35a) 72 pages.
Estavão-Costa et al., "Delayed Gastric Emptying and Gastroesophageal Reflux: A Pathophysiologic Relationship", J. of Pediatric Gastroenterology and Nutrition, pp. 471-474 (2001).
Evans et al., "Gastroparesis and Small Bowel Dysmotility in Irritable Bowel Syndrome", Dig Dis Sci, 42:2087-2093 (1997).
Evans et al., "Jejunal Sensorimotor Dysfunction in Irritable Bowel Syndrome: Clinical and Psychosocial Features", Gastroenterol, 110:393-404 (1996).
Faris et al., "Effect of Decreasing Afferent Vagal Activity with Ondansetron on Symptoms of Bulimia Nervosa: a Randomized, Double-Blind Trial", The Lancet, pp. 792-797 (2000).
Furukawa et al., "Effects of Selective Vagal Stimulation on the Gallbladder and Sphincter of Oddi and Peripheral Vagal Routes Mediating Bile Evacuative Responses Induced by Hypothalamic Stimulation", JJP, 42:321-334 (1992).
George et al., "Vagus Nerve Stimulation Therapy", Neurology, 59(Supp 4):S56-S61 (2002).
Gershon, "The Second Brain", Harper Collins Publishers, Inc, New York, Ny p. 19 (1998).
Görtz et al., "A Five- to Eight-Year Follow-up Study of Truncal Vagotomy as a Treatment for Morbid Obesity", Proceedings of the Third Annual Meeting, American Society for Bariatric Surgery, p. 145 (1986) (Abstract).
Görtz et al., "Truncal Vagotomy Reduces Food and Liquid Intake in Man", Physiology & Behavior, 48:779-781 (1990).
Greydanus et al., "Neurohormonal Factors in Functional Dyspepsia: Insights on Pathophysiological Mechanisms", American Gastroenterological Association, 100(5):1311-1318 (1991).
Grossi et al., "Swallows, Oesophageal and Gastric Motility in Normal Subjects and in Patients with Gastro-Oesophageal Reflux Disease: a 24-h pH-Manometric Study", Neurogastroenterology and Motility, pp. 115-121 (1998).
Guyton et al., "Propulsion and Mixing of Food in the Alimentary Tract", Textbook of Medical Physiology, $10^{th}$ ed. Philadelphia: W. B. Saunders and Company, 200:728-734 (2000).
Guyton et al., "Secretory Functions of the Alimentary Tract", Textbook of Medical Physiology, $10^{th}$ ed. Philadelphia: W. B. Saunders and Company, 200:738-753 (2000).
Hausken et al., "Low Vagal Tone and Antral Dysmotility in Patients with Functional Dyspepsia", Psychosomatic Medicine, 55:12-22 (1993).
Heitkemper et al., "Evidence for Automatic Nervous System Imbalance in Women with Irritable Bowel Syndrome", Digestive Diseases and Sciences, 43(9):2093-2098 (1998).
Herrera et al., "Intermittent Vagal Blocking with an Implantable Device Reduces Maximum Tolerated Volume (MTV) During a Standardized Nutrient Drink Test in Obese Subjects", AGA Institute, AASLD, SSAT, The 110th Annual Meeting of the AGA Institute: Digestive Disease Week May 30-Jun. 4, 2009, Chicago, IL, Gastroenterology, 136(5)(Supp. 1) (May 2009).
Herrera et al., "Intermittent Vagal Blockade with an Implantable Device Improves Glycemic Control in Obese subjects with Type 2 Diabetes", 2009 Poster Session / Supplement to Surgery for Obesity and Related Diseases, Official Journal of the American Society for Bariatric Surgery, 5(3S):S48-S49, (May/Jun. 2009).
Herrera et al., "VBLOC and Improvements in Co-Morbidities in Obese Subjects During Weight Loss", Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, 19(8):983-984, (Aug. 2009).
Herrera et al., "Intermittent Vagal Blocking with an Implantable Device Reduces Maximum Tolerated Volume (MTV) During a Standardized Nutrient Drink Test in Obese Subjects", Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, 19(8):1012 (Aug. 2009).
Herrera et al., "Vagal Blocking Improves Glycemic Control and Blood Pressure in Subjects with Type 2 Diabetes and Hypertension", 2010 Plenary Session / Supplement to Surgery for Obesity and Related Diseases, Official Journal of the American Society for Bariatric Surgery, 2(3):S1-S26, (May/Jun. 2010).
Herrera et al., "Treatment of Obesity-Related Type 2 Diabetes with Vagal Blocking", Obesity 2011 Abstract Supplement / Poster Abstracts—Monday, Oct. 3, 2011, Obesity, 19(Supp. 1):S185, (Nov. 2011), www.obsesityjournal.org.
Hjelland et al., "Vagal tone and meal-induced abdominal symptoms in healthy subjects", Digestion, 65:172-176 (2002).
Holst et al., "Nervous Control of Pancreatic Exocrine Secretion in Pigs", Acta Physiol. Scand., 105:33-51 (1979).
Holst et al., "Nervous control of pancreatic endocrine secretion in pigs" Acta Physiol Scand, 111:1-7 (1981).
Hornbuckle et al. "The Diagnosis and Work-Up of the Patient with Gastroparesis", J Clin Gastroenterol, 30:117-124 (2000).
Hunt, "The Relationship Between the Control of pH and Healing and Symptom Relief in Gastro-Oesophageal Reflux Disease", Ailment Pharmacol Ther., 9(Suppl. 1):3-7 (1995).
ICD-10, "Classification of Mental and Behavioural Disorders", World Health Organization, 2 pages (1992), printed from http://www.mental-health-matters.com/disorders/dis_details.
International Search Report (Partial) mailed Aug. 28, 2008.
International Search Report and Written Opinion mailed Jul. 8, 2009.
International Search Report and Written Opinion mailed Nov. 29, 2006.
International Search Report and Written Opinion mailed Dec. 9, 2011.
Kaiser, "Gallstone Ileus", New England J. of Medicine, 336(12):879-880 (correspondence) (1997).
Kaminski et al., "The Effect of Electrical Vagal Stimulation on Canine Pancreatic Exocrine Function", Surgery, pp. 545-552 (1975).
Kellow et al., "Dysmotility of the Small Intestine in Irritable Bowel Syndrome", Gut, 29:1236-1243 (1988).
Kellow et al., "Rome II: A Multinational Consensus Document on Gastrointestinal Disorders—Principles of Applied Neurogastroenterology: Physiology/Motility-Sensation", Gut, 45(Suppl II):II17-II24 (1999).
Kilgore et al., "Nerve Conduction Block Utilising High-Frequency Alternating Current", Medical & Biological Engineering & Computing, 42:394-406 (2004).
Kow et al., "An Implantable Vagal Blocking System to Treat Obesity: Laparoscopic Implantation Technique and Early Results in a proof-of-Principle Clinical Study", SAGES 2008 Emerging Technology Oral Abstracts, p. 295, www.sages.org.
Kow et al., "Comparison of Food Ingestion Disorders with Three Devices for Obesity," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, 18(8):914-915 (Aug. 2008).
Kow et. al. "Selecting Vagal Blocking Electrical Algorithms for Obesity Treatment", Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, 18(8):924, (Aug. 2008).
Kow et al., "Comparison of Food Ingestion disorders with Three Devices for Obesity Treatment", and Wilson, Richard, et al., "Intraabdominal Vagal Blocking Reduces Body Weight with Associated Reductions in Heart Rate and Without Adverse Effects on Electrocardiographic Parameters", TOS 2008 Abstract Supplement / Poster Session 2 Abstracts, 16(Supp. 1):S222, (Oct. 2008) www.obesityjournal.org.

(56) References Cited

OTHER PUBLICATIONS

Kow et al., "Vagal Blocking Improves Obesity-Related Co-Morbidities in Obese Subjects with type 2 Diabetes Mellitus", 23rd Annual Scientific Conference of the Obesity Surgery Society of Australia and New Zealand , OSSANZ Conference 2010: The Changing Shape of Bariatrics, Nov. 10-12, Wednesday Nov. 10 3:30 pm-5:00 pm, Tasmania Hotel Grand Chancellor, Hobart, Conference Program Handbook.
Kow et al., "Vagal Blocking for the Treatment of Obesity Delivered Using the Fully Implantable Maestro Rechargeable System: 12 Month Results", Surgery for Obesity and Related Diseases: Emerging Technologies Session 2011, 7:363-364, (2011).
Koren et al., "Vagus Nerve Stimulation Does Not Lead to Significant Changes in Body Weight in Patients With Epilepsy", Epilepsy & Behavior, 8:246-249 (2006).
Koren et al., "To Eat or Not to Eat—How the Gut Talks to the Brain", New England J. Med., pp. 926-928 (Sep. 4, 2003).
Kosel et al., "Beyond the Treatment of Epilepsy: New Applications of Vagus Nerve Stimulation in Psychiatry", CNS Spectrums, 8(7):515-521 (Jul. 2003).
Kral, "Vagotomy as a Treatment for Morbid Obesity", Surg. Clinics of N. Amer., 59(6):1131-1138 (1979).
Kral, "Vagotomy for Treatment of Severe Obesity", The Lancet, pp. 307-308 (1978).
Kral et al., "Gastroplasty for Obesity: Long-Term Weight Loss Improved by Vagotomy", World J. Surg., 17:75-79 (1993).
Lagergren et al., "Symptomatic Gastroesophageal Reflux as a Risk Factor for Esophageal Adenocarcinoma", New Engl J Med, 340:825-829, 831(1999).
Layer et al., "Human pancreatic secretion during phase II antral motility of the interdigestive cycle", American Physiological Society, 88:G249-G253 (1988).
Lin et al., "Hardware-software co-design of portable functional gastrointestinal stimulator system", J. of Medical Eng. & Tech., 27(4):164-177 (2003).
Long, editor, Chapter 3, "The Stomach", Gastrointestinal System, $2^{nd}$ Ed., Mosby Publisher, London (2002).
Long, editor, Chapter 4, "The Liver and Biliary Tract", Gastrointestinal System, $2^{nd}$ Ed., Mosby Publisher, London (2002).
Mabayo et al., "Inhibition of Food Passage by Osmeprazole in the Chicken", European J. of Pharmacology, pp. 161-165 (1995).
Martin-Portugues et al., "Histopathologic Features of the Vagus Nerve After Electrical Stimulation in Swine", Histol Histopathol, 20:851-856 (2005).
Medical Encyclopedia: Anorexia Nervosa, U.S. National Library of Medicine and National Institutes of Health, pp. 1-3 (Jun. 22, 2004) printed from http://www.nlm.nih.gov/medlineplus/print/ency/article/000362.htm, Jun. 6, 2006.
Merio et al., "Slow Gastric Emptying in Type 1 Diabetes: Relation to Autonomic and Peripheral Neuropathy, Blood Glucose, and Glycemic Control", Diabetes Care, 20:419-423 (1997).
Mintchev et al., "Electrogastrographic impact of multi-site functional gastric electrical stimulation", J. of Medical Eng. & Tech., 23(1):5-9 (1999).
Mittal et al., "Mechanism of Disease: The Esophagogastric Junction", New Engl J Med, 336:924-927, 929-932 (1997).
Netter, "Atlas of Human Anatomy", 3rd Ed., Plate 120, (Icon Learning Systems, New Jersey) (2003).
Norton et al., "Optimizing Outcomes in Acute Pancreatitis", Drugs, 61(11):1581-1591 (2001).
Novartis product description, Zelnorm®, Jul. 2002 (T2002-19).
O'Brien et al., "The Laparoscopic Adjustable Gastric Band (Lap-Band®): A Prospective Study of Medium-Term Effects on Weight, Health and Quality of Life", Obesity Surgery, 12:652-660 (2002).
Owyang, "Negative Feedback Control of Exocrine Pancreatic Secretion: Role of Cholecystokinin and Cholinergic Pathway", Symposium: Physiology of Cholecystokinin, American Institute of Nutrition, pp. 1321S-1326S (1994).
Paterson et al., "Determinants of Occurrence and Volume of Transpyloric Flow During Gastric Emptying of Liquids in Dogs: Importance of Vagal Input", Dig Dis Sci, 45:1509-1516 (2000).
Peeters et al., "Obesity in Adulthood and Its Consequences for Life Expectancy: A Life Table Analysis", Annals of Internal Medicine, 138(1):24-32 (2003).
Petrofsky et al., "Impact of Recruitment Order on Electrode Design for Neural Prosthetics of Skeletal Muscle", Am. J. of Physical Medicine, 60(5):243-253 (1981).
Poelmans et al., "Prospective Study on the Incidence of Chronic Ear Complaints Related to Gastroesophageal Reflux and on the Outcome of Antireflux Therapy", Ann Otol Rhinol Laryngol, 111:933-938(2002).
Product Brochure, "ATROSTIM Phrenic Nerve Stimulator," AtroTech Oy, P.O. Box 28, FIN-33721 Tampere, Finland, 2 pages (Jun. 2004).
Rashev et al., "Microprocessor-Controlled Colonic Peristalsis", Digestive Diseases and Sciences, 47(5):1034-1048 (2002).
Rashev et al., "Three-dimensional static parametric modelling of phasic colonic contractions for the purpose of microprocessor-controlled functional stimulation", J. of Medical Eng. & Tech., 25(3):85-96 (2001).
Rasmussen et al., "A Double-Blind Placebo-Controlled Study on the Effects of Omeprazole on Gut Hormone Secretion and Gastric Emptying Rate", Scand. J. Gastroenterol, pp. 900-905 (1997).
Rösch et al., "Frequency-Dependent Secretion of Pancreatic Amylase, Lipase, Trypsin, and Chymotrypsin During Vagal Stimulation in Rats", Pancreas, pp. 499-506 (1990).
Roslin et al., "The Use of Electrical Stimulation of the Vagus Nerve to Treat Morbid Obesity", Epilepsy & Behavior, 2:S11-S16 at p. S13 (2001).
Roslin et al., "Vagus Nerve Stimulation in the Treatment of Morbid Obesity", Ch. 6 to Vagus Nerve Stimulation, $2^{nd}$ Ed., pp. 113-121 (Schlachter et al. ed., Martin Dunitz), 2003.
Sarnelli et al., "Symptoms Associated with Impaired Gastric Emptying of Solids and Liquids in Functional Dyspepsia", Am J Gastroenterol, 98:783-788 (2003).
Sarr et al., "The EMPOWER Study: Randomized, Prospective, Double-Blind, Multicenter Trial of Vagal Blockade to Induce Weight Loss in Morbid Obesity", Obes. Surg, pp. 12 (Sep. 8, 2012).
Schapiro et al., "Neurohypophyseal Regulation of the Exocrine Pancreas", Amer. J. of Gastroenterology, pp. 587-591 (1979).
Scheffer et al., "Elicitation of Transient Lower Oesophageal Sphincter Relaxations in Response to Gastric Distension", Neurogastroenterol Motil, 14:647-651, 654 (2002).
Schmidt et al., "Ambulatory 24-Hour Jejunal Motility in Diarrhea-Predominant Irritable Bowel Syndrome", J Gastroenterol, 31:581-584, 586-589 (1996).
Schwartz et al., "Chemospecific Alterations in Duodenal Perception and Motor Response in Functional Dyspepsia", Am J Gastroenterol, 96:2596-2602 (2001).
Schwartz et al., "Human Duodenal Motor Activity in Response to Acid and Different Nutrients", Dig Dis Sci, 46:1472-1481 (2001).
Shikora, "'What are the Yanks Doing' The U.S. Experience with Implantable Gastric Stimulation (IGS) for the Treatment of Obesity—Update on the Ongoing Clinical Trials", Obesity Surgery, 14(Suppl):S40-S48 (2004).
Simren et al., "Abnormal Propagation Pattern of Duodenal Pressure Waves in the Irritable Bowel Syndrome (IBS)", Dig Dis Sci, 45:2151-2159, 2161 (2000).
Smith et al., "Truncal Vagotomy in Hypothalamic Obesity", The Lancet, pp. 1330-1331 (1983).
Solomonow et al., "Control of Muscle Contractile Force through Indirect High-Frequency Stimulation", Am._J. of Physical Medicine, 62(2):71-82 (1983).
Sontag et al., "Asthmatics with Gastroesophageal Reflux: Long Term Results of a Randomized Trial of Medical and Surgical Antireflux Therapies", Am J Gastroenterol, 98:987-999 (2003).
Soran et al., "Outcome and quality of life of patients with acute pancreatitis requiring intensive care", J. Surg. Res., 91(1):89-94 (2000).

(56) References Cited

OTHER PUBLICATIONS

Stanghellini et al., "Risk Indicators of Delayed Gastric Emptying of Solids in Patients with Functional Dyspepsia", Gastroenterol, 110:1036-1042 (1996).
Steer et al., "Chronic Pancreatitis", New England J. of Medicine, pp. 1482-1490 (1995).
Steinbrook, "An Opioid Antagonist for Postoperative Ileus", New England J. of Medicine, 345(13):988-989 (2001) (Editorial).
Steinbrook, "Surgery for Severe Obesity", New England J. Med., 350:1075-1079 (2004).
Tack et al., "Role of Impaired Gastric Accommodation to a Meal in Functional Dyspepsia", Gastroenterol, 115:1346-1352 (1998).
Tack et al., "Symptom Pattern and Gastric Emptying Rate Assessed by the Octanoic Acid Breath Test in Functional Dyspepsia" [abstract]. Gastroenterol, 114:A301 (1998).
Taguchi et al., "Selective Postoperative Inhibition of Gastrointestinal Opioid Receptors", New England J. of Medicine, 345(13):935-940 (2001).
Talley et al., "Rome II: A Multinational Consensus Document on Gastrointestinal Disorders—Functional Gastroduodenal Disorders" Gut, 45(Suppl II):II37-II42 (1999).
Taylor et al., "Effects of Pancreatic Polypeptide, Caerulein, and Bombesin on Satiety in Obese Mice", American Journal of Physiology, 248:G277-G280 (1985).
Thompson et al., "Rome II: A Multinational Consensus Document on Gastrointestinal Disorders—Functional Bowel Disorders and Functional Abdominal Pain", Gut, 45(Supp II):II43-II47 (1999).
Tiscornia et al., "Neural Control of the Exocrine Pancreas: An Analysis of the Cholinergic, Adrenergic, and Peptidergic Pathways and Their Positive and Negative Components 1: Neural Mechanisms", Mount Sinai J. of Medicine, pp. 366-383 (1987).
Toouli et al., "Vagal Blocking for Obesity Control (VBLOC): Effects on Excess Weight Loss, Calorie Intake, Satiation and Satiety", Obesity Surgery: Including Laparoscopy and Allied Care, Program Issue, World Congress, Porto, Sep. 5 to 8, 2007. An International Surgical Journal for Research and Treatment of Massive Obesity, 17(8)(Abstract No. 83):1043 (Aug. 2007).
Toouli et al., "Vagal Blocking for Obesity Control (VBLOC): Interim Six Months Results in an ongoing Trial Using a Second Generation System", 2008 Scientific Session of the Society of American Gastrointestinal and Endoscopic (SAGES), Philadelphia, Pennsylvania, USA Apr. 9-12, 2008. Poster Presentations, Surgical Endoscopy (2008) 22:S194, (2008).
Toouli et al., "Intra-Abdominal Vagal Blocking Reduces Calorie Intake, Enhances Satiation and Reduces Hunger during Significant and Sustained Weight Loss in Obese Subjects," Digestive Disease Week and the 109th Annual Meeting of the AGA Institute: May 17-22, 2008, San Diego, CA, Gastroenterology, 134(4)(Suppl. 1):A-370 (Apr. 2008).
Toouli et al., "Vagal Blocking for Obesity Control (VBLOCTM): Ongoing Comparison of Weight Loss with Two Generations of an Active, Implantable Medical Device", 2008 Plenary Session II / Surgery for Obesity and Related Diseases, Official Journal of the American Society for Bariatric Surgery et al., 4(3):305 (May/Jun. 2008).
Toouli et al., "Reduced Calorie Intake and Weight Loss During Vagal Bloc (VBLOC Therapy) in Morbidly Obese Patients with Type 2 Diabetes Mellitus", Gastroenterology, 140:S-619, AGA Institute (2011).
Toouli et al., "Treatment of Obesity-Related Co-Morbidities with VBLOC Therapy", Obes. Surg. 21:998 (2011).
Toouli et al., "Vagal Blocking: Treatment of Obesity Related type 2 Diabetes and blood Pressure—18 Month Results", 24th Annual Scientific Conference of the Obesity Surgery Society of Australia and New Zealand, OSSANZ Conference 2012: Bariatric surgery—more than an operation, Apr. 11-13, Wednesday Nov. 11 3:30 pm-5:00 pm, Northern Territory Darwin Convention Centre, Darwin, Conference Program Handbook.
Tougas, "The Autonomic Nervous System in Functional Bowel Disorders", Gut, 47(Suppl IV):iv78-iv80 (2000).
Tweden et al., "Vagal Blocking for Obesity Control (VBLOC): Concordance of Effects of Very High Frequency Blocking Current at the Neural and Organ Levels Using Two Preclinical Models", Gastroenterology, 130(Supp 2 2):A-148, AGA Institute. (2006).
Tweden et al., "Vagal Blocking for Obesity Control (VBLOC): Concordance of Effects of Very High Frequency Blocking Current at the Neural and Organ Levels Using Two Preclinical Models", Gastroenterology, 130(4)(Suppl. 2)(Abstract No. 951):A-148 (Apr. 2006).
Tweden et al., "Vagal Blocking for Obesity Control (VBLOC): Studies of Pancreatic and Gastric Function and Safety in a Porcine Model", Plenary Session 2006/2 Surgery for Obesity and Related Diseases, Official Journal of the American Society for Bariatric Surgery, 2(3):301-302 (May/Jun. 2006).
Tweden et al., "Vagal Blocking for Obesity Control (VBLOC): Studies of Pancreatic Function and Safety in a Porcine Model", Obesity Surgery: Including Laparoscopy and Allied Care, Program Issue, World Congress, Australia, Aug. 30-Sep. 2, 2006. An International Surgical Journal for Research and Treatment of Massive Obesity, 16(8):988 (Aug. 2006).
Tweden et al., "Vagal Blocking Treatment of Obesity Related Type 2 Diabetes and Blood Pressure—18 Month Results", 5th Congress of the International Federation for the surgery of Obesity and Metabolic Disorders European Chapter (IFSO-EC), Barcelona '12, (Apr. 26-28, 2012).
Tzu-Ming et al., "Long-Term Results of Duodenectomy with Highly Selective Vagotomy in the Treatment of complicated Duodenal Ulcers", Amer. J. of Surg., 181:372-376 (2001).
Undeland et al., "Wide Gastric Antrum and Low Vagal Tone in Patients with Diabetes Mellitus Type 1 Compared to Patients with Functional Dyspepsia and Healthy Individuals", Dig Dis Sci, 41:9-16 (1996).
U.S. Appl. No. 13/178,221, filed Jul. 7, 2011.
U.S. Appl. No. 13/188,293, filed Jul. 21, 2011.
U.S. Appl. No. 12/908,375, filed Oct. 20, 2010.
U.S. Appl. No. 12,638,266, filed Dec. 15, 2009.
U.S. Appl. No. 11/943,069, filed Nov. 20, 2007.
U.S. Appl. No. 11/943,093, filed Nov. 20, 2007.
U.S. Appl. No. 11/943,054, filed Nov. 20, 2007.
Van Den Honert et al., "Generation of Unidirectionally Propagated Action Potentials in a Peripheral Nerve by Brief Stimuli", Science, 206:1311-1312 (1979).
Van Wijk et al., "Gastric Emptying and Dyspeptic Symptoms in the Irritable Bowel Syndrome", Scand J Gastroenterol, 27:99-100, 101 (1992).
Vassallo et al., "Colonic Tone and Motility in Patients with Irritable Bowel Syndrome", Mayo Clin Proc, 67:725-727, 729-731 (1992).
Waataja et al., "Effects of High-Frequency Alternating Current on Axonal Conduction Through the Vagus Nerve", Journal of Neural Engineering Neural Eng. 8:1741-1747 (2011) online at stacks.iop.org.
Wray, N., et al., "Reduced Calorie Intake and Weight Loss During Vagal Blocking in Subjects with Obesity-Related Type 2 Diabetes Mellitus," Obesity 2011 Abstract Supplement / Poster Abstracts— Monday, Oct. 3, 2011, Obesity, (19)(Supp. 1):S190, (Nov. 2011), www.obesityjournal.org.
Wilmer et al., "Ambulatory Gastrojejunal Manometry in Severe Motility-like Dyspepsia: Lack of Correlation between Dysmotility, Symptoms and Gastric Emptying", Gut, 42:235-242 (1998).
Wilson et al., "Intra-Abdominal Vagal Blocking Re3duces body Weight with Associated Reductions in Heart Rate and Without Adverse Effects on Electrocardiographic Parameters", Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, 18(8):923 (Aug. 2008).
Yoshinaga et al., "Cholecystokinin Acts as an Essential Factor in the Exacerbation of Pancreatic Bile Duct Ligation-Induced Rat Pancreatitis Model Under Non-Fasting Condition", Japanese J Pharmacol, 84:44-50 (2000).
Zapater et al., "Do Muscarinic Receptors Play a Role in Acute Pancreatitis?", Clin. Drug Invest., 20(6):401-408 (2000).

* cited by examiner

Mode 1: High frequency with pulse width < period

Frequency 150 – 10,000 Hz
0.01 milliseconds < Pulse Width < Period

Mode 2: Mode 1 followed by low frequency pulses

Mode 3: Mode 1 applied at short bursts

NEURAL MODULATION DEVICES AND METHODS

CROSS-REFERENCE TO RELATED APPLICATIONS

This application is a divisional of U.S. patent application Ser. No. 13/154,846, filed Jun. 7, 2011, now U.S. Pat. No. 8,825,164, issued Sep. 2, 2014, which claims benefit of Provisional Application No. 61/353,850, filed Jun. 11, 2010, which applications are incorporated herein by reference.

BACKGROUND OF THE INVENTION

1. Field of the Invention

This invention pertains to devices and methods for neuromodulation for gastrointestinal disorders and conditions associated with excess weight.

2. Background

Obesity and other eating disorders are serious health conditions that lead to increased morbidity and mortality. Over the last decade, the prevalence of obesity has increased more than 80%, representing an estimated 43 million adults in 2002. (Mokdad A H, et al, The spread of the obesity epidemic in the United States, 1991-1998. JAMA 1999; (282):1519-22). In terms of mortality, an estimated 280,000 to 325,000 adults in the United States die each year from causes related to obesity. (Allison D B et al, Annual deaths attributable to obesity in the United States. JAMA 1999; 282:1530-8). More importantly, excess weight has been positively correlated with years of life lost. (Fontaine K R et al., Years of life lost due to obesity. JAMA 2003; (289):187-93).

In addition to mortality, substantial morbidity is associated with obesity. For example, in 2000, the total cost of obesity in the United States was estimated to be $117 billion ($61 billion in direct medical costs, $56 billion in indirect costs). (U.S. Department of Health and Human Services. The Surgeon General's call to action to prevent and decrease overweight and obesity. Rockville (Md.): U.S. Department of Health and Human Services, Public Health Service, Office of the Surgeon General; 2001). An estimated 9.1% of annual medical spending in the United States is attributed to overweight and obesity—a figure that rivals medical costs attributable to cigarette smoking. In addition, many other conditions are found in patients that have excess weight including hypertension and diabetes.

Thus, there remains a need to develop effective treatments for gastrointestinal conditions and conditions associated with excess weight.

SUMMARY

This disclosure is directed to systems and methods for treating gastrointestinal disorders and/or a condition associated with excess weight in a subject. Conditions associated with excess weight include obesity, metabolic syndrome, type II diabetes, prediabetes, hypertension, bulimia, compulsive eating, and gall bladder disease. Gastrointestinal disorders include gastrointestinal disorders that can be treated by at least partial down regulation of neural activity on the vagus nerve including inflammatory bowel disease, pancreatitis, and irritable bowel syndrome. Gastrointestinal disorders also include gastrointestinal disorders that can be treated by up-regulation, or at least partial down-regulation of other nerves (e.g. the splanchnic, or celiac nerves), alone, or in combination with up-regulation or at least partial down-regulation of the vagus nerve.

An aspect of the disclosure provides a system for treating a gastrointestinal disorder or a condition associated with excess weight of a subject comprising at least one electrode configured to be implanted within a body of the patient and placed at a vagus nerve, the electrode also configured to apply therapy to the vagus nerve upon application of a therapy cycle to the electrode; an implantable neuroregulator for placement in the body of the patient beneath the skin layer, the implantable neuroregulator being configured to generate a therapy cycle, wherein the therapy cycle comprises an electrical signal comprising: a set of pulses applied at a first selected frequency of about 150-10,000 Hz, and wherein each pulse of the set of pulses has a pulse width of at least 0.01 milliseconds and less than the period of the first selected frequency.

In other embodiments, the therapy cycle comprises at least one electrical signal that comprises a pulse or set of pulses that have a first selected frequency of about 150 Hz or greater; and a total amount of charge delivered to the nerve of about 5 microcoulombs to 200,000 microcoulombs during the therapy cycle. In embodiments, the therapy cycle is a low charge therapy cycle.

Another aspect of the disclosure provides methods for selecting a therapy cycle for an implantable device in a subject. In one embodiment, the method comprises selecting parameters for a therapy cycle for an implantable device in a subject comprising: selecting parameters of a therapy cycle, wherein the therapy cycle comprises an electrical signal comprising: i) a set of pulses applied at a first selected frequency of about 150-10,000 Hz, and wherein each pulse of the set of pulses has a pulse width of at least 0.01 milliseconds and less than the period of the first selected frequency; communicating the selected parameters to the implantable device comprising the system of claim 1; and determining the amount of actual therapy delivered over a time period and adjusting the parameters of the therapy cycle to achieve delivery of at least 6 hours of treatment or adjusting the parameters of the therapy cycle or both to increase the amount of excess weight loss, to affect the blood pressure, and/or diabetes of the subject.

Another aspect of the disclosure provides a method of treating a gastrointestinal disorder or a condition associated with excess weight in a subject comprising applying an electrode to a vagus nerve at a location below vagal innervation of the heart; applying a therapy cycle to the vagus nerve, wherein each therapy cycle comprises a high frequency electrical signal having a first selected frequency of at least 150 Hz, a low frequency electrical signal having a second selected frequency of less than 150 Hz, an on period of at least 30 seconds, and an off period, wherein the off period is selected to allow at least partial recovery of neural activity. In some embodiments, the method further comprises administering an agent that treats the gastrointestinal condition, affects weight loss, blood pressure, or diabetes. Agents that affect weight loss include but are not limited to agents that enhance the sensation of satiety, agents that decrease appetite, agents that block the absorption of fat or other nutrients, agents that inhibit enzymes that digest fat, agents that are thermogenic, or combinations thereof.

DETAILED DESCRIPTION

A. Description of Vagal Innervation of the Alimentary Tract

Figure 1:
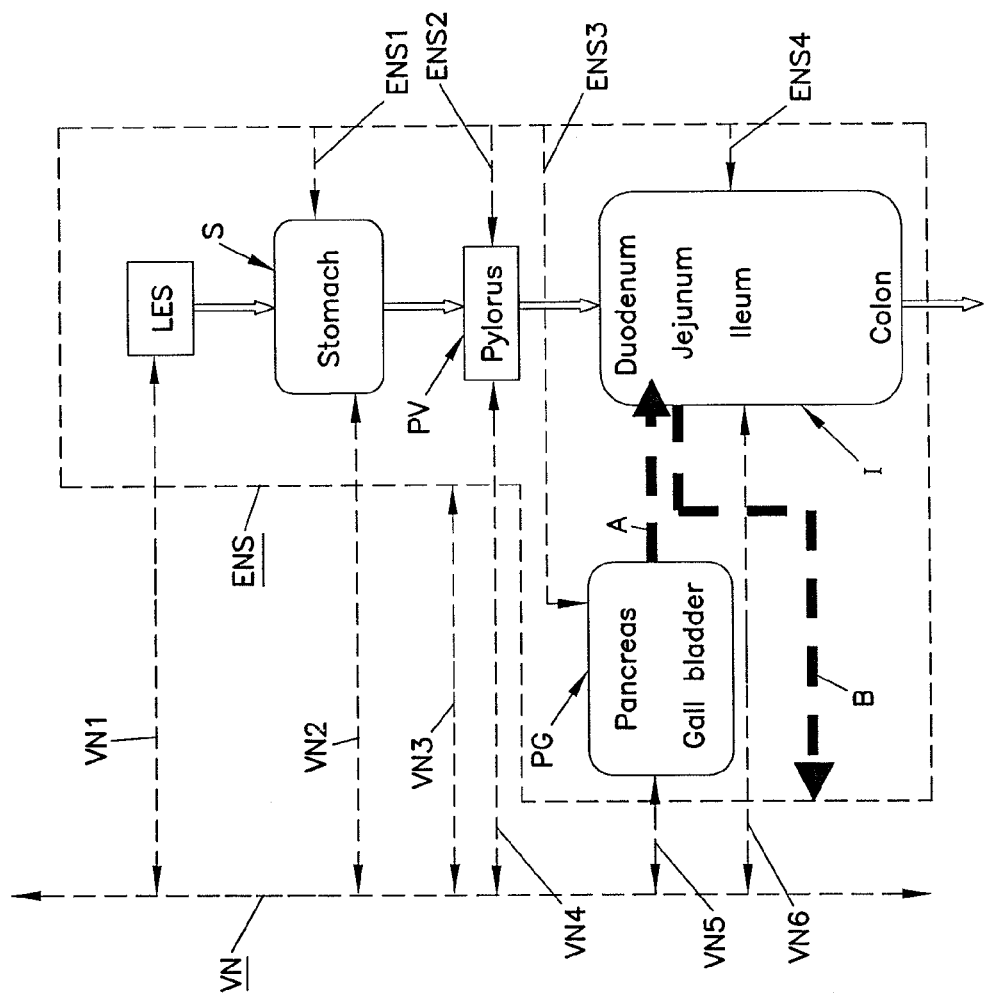
FIG. 1 is a schematic illustration of an alimentary tract (GI tract plus non-GI organs such as the pancreas and liver) and its relation to vagal and enteric innervation.

FIG. 1 is a schematic illustration of an alimentary tract (GI tract plus non-GI organs such as the pancreas and gall bladder, collectively labeled PG) and its relation to vagal and enteric innervation. The lower esophageal sphincter (LES) acts as a gate to pass food into the stomach S and, assuming adequate function of all components, prevent reflux. The pylorus PV controls passage of chyme from the stomach S into the intestines I (collectively shown in the figures and including the large intestine or colon and the small intestine including the duodenum, jejunum and ileum). The biochemistry of the contents of the intestines I is influenced by the pancreas P and gall bladder PG which discharge into the duodenum. This discharge is illustrated by dotted arrow A.

Figure 2:
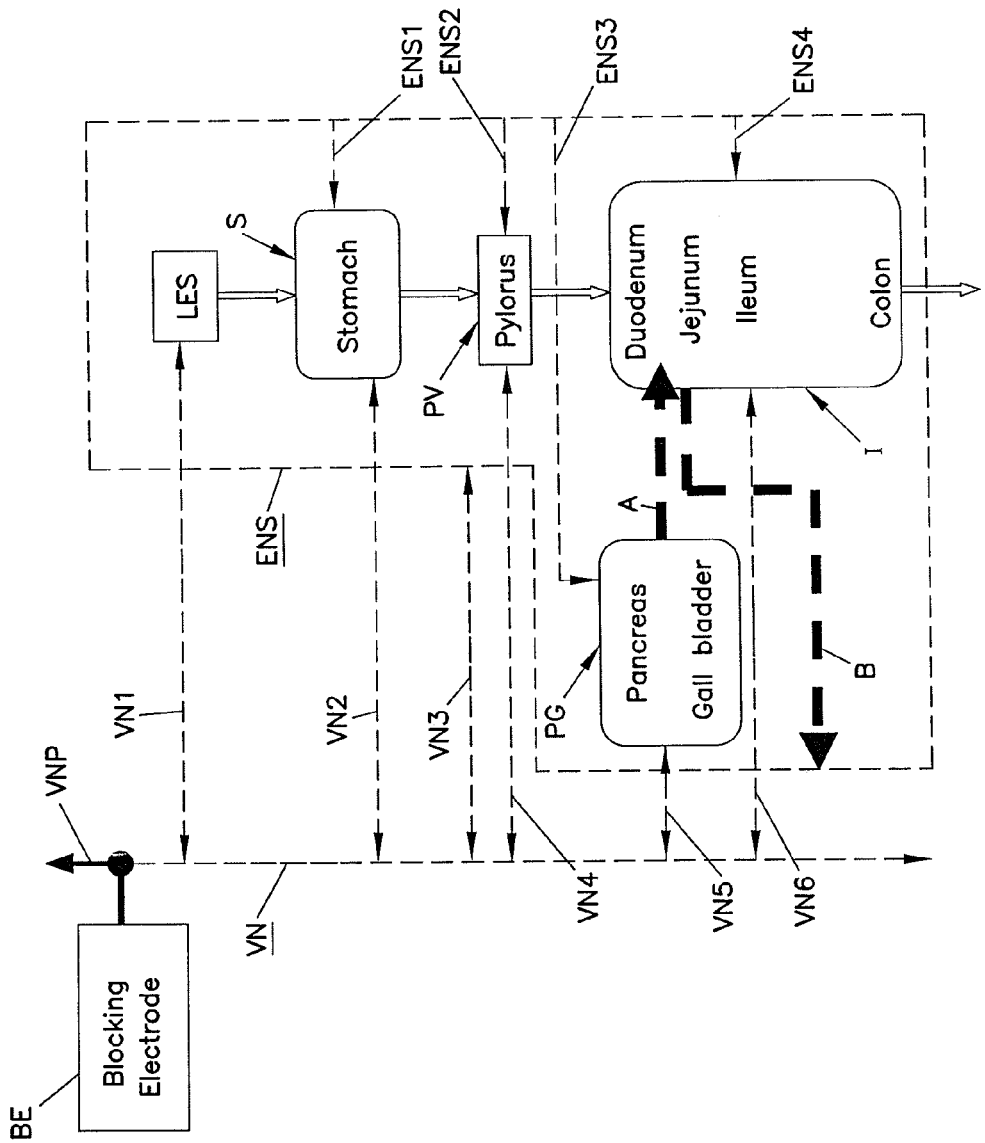
FIG. 2 is the view of FIG. 1 showing the application of an electrode to the vagus nerve.

The vagus nerve VN transmits signals to the stomach S, pylorus PV, pancreas and gall bladder PG directly. Originating in the brain, there is a common vagus nerve VN in the region of the diaphragm (not shown). In the region of the diaphragm, the vagus VN separates into anterior and posterior components with both acting to innervate the GI tract. In FIGS. 1, and 2, the anterior and posterior vagus nerves are not shown separately. Instead, the vagus nerve VN is shown schematically to include both anterior and posterior nerves. The vagus nerve VN contains both afferent and efferent components sending signals to and away from, respectively, its innervated organs.

In addition to influence from the vagus nerve VN, the GI and alimentary tracts are greatly influenced by the enteric nervous system ENS. The enteric nervous system ENS is an interconnected network of nerves, receptors and actuators throughout the GI tract and pancreas and gall bladder PG. There are many millions of nerve endings of the enteric nervous system ENS in the tissues of the GI organs. For ease of illustration, the enteric nervous system ENS is illustrated as a line enveloping the organs innervated by the enteric nervous system ENS. The vagus nerve VN innervates, at least in part, the enteric nervous system ENS (schematically illustrated by vagal trunk VN3 which represents many vagus-ENS innervation throughout the gut). Also, receptors in the intestines I connect to the enteric nervous system ENS. Arrow B in the figures illustrates the influence of duodenal contents on the enteric nervous system ENS as a feedback to the secretion function of the pancreas, liver and gall bladder. Specifically, receptors in the intestine I respond to the biochemistry of the intestine contents (which are chemically modulated by the pancreao-biliary output of Arrow A). This biochemistry includes pH and osmolality.

In FIGS. 1 and 2, vagal trunks VN1, VN2, VN4 and VN6 illustrate schematically the direct vagal innervation of the GI organs of the LES, stomach S, pylorus PV and intestines I. Trunk VN3 illustrates direct communication between the vagus VN and the ENS. Trunk VN5 illustrates direct vagal innervation of the pancreas and gall bladder. Enteric nerves ENS1-ENS4 represent the multitude of enteric nerves in the stomach S, pylorus PV, pancreas and gall bladder PG and intestines I.

While communicating with the vagus nerve VN, the enteric nervous system ENS can act independently of the vagus and the central nervous system. For example, in patients with a severed vagus nerve (vagotomy—a historical procedure for treating ulcers), the enteric nervous system can operate the gut. Most enteric nerve cells are not directly innervated by the vagus. Gershon, "The Second Brain", Harper Collins Publishers, Inc, New York, N.Y. p. 19 (1998).

B. Therapy Delivery system

The disclosure provides systems for treating a gastrointestinal condition or a condition associated with excess weight comprising a neuroregulator that provides signals to modulate neural activity on the vagus nerve. In an embodiment, a system (schematically shown in FIG. 3) for designing a therapy or for treating such conditions including obesity, hypertension, diabetes or other gastrointestinal disorders includes a neuroregulator 104, and at least one electrode, and in some embodiments, two electrical lead assemblies 106, 106a, each comprising an electrode. In some embodiments, the neuroregulator comprises a power source. In an embodiment, the power source is a secondary (rechargeable) battery or a primary (non-rechargeable) battery. In other embodiments, the neuroregulator does not contain a battery, and power is provided from an external source via radio-frequency energy. In further embodiments, the neuroregulator contains a primary or secondary battery, and can be powered either by the battery, or by power is provided from an external source via radio-frequency energy. The neuroregulator 104 is adapted for implantation within a patient. As will be more fully described herein, the neuroregulator 104 typically is implanted just beneath a skin layer 103.

The neuroregulator 104 is configured to connect electrically to the electrode via one or more electrical lead assemblies 106,106a. In some embodiments, the lead assemblies 106, 106a are electrically connected to the circuitry of the neuroregulator 104 by conductors 114, 114a. Industry standard connectors 122, 122a are provided for connecting the lead assemblies 106, 106a to the conductors 114, 114a. As a result, leads 116, 116a and the neuroregulator 104 may be separately implanted. Also, following implantation, lead 116, 116a may be left in place while the originally placed neuroregulator 104 is replaced by a different neuroregulator. The neuroregulator 104 generates a therapy cycle including a therapy signal and transmits the therapy signal to the lead assemblies 106, 106a.

The therapy cycle up-regulates and/or down-regulates activity on the nerves of a patient based on the therapy signals provided by the neuroregulator 104. In an embodiment, the lead assemblies 106, 106a include distal electrodes 212, 212a, which are placed on one or more nerves of a patient. For example, the electrodes 212, 212a may be individually placed on the anterior vagal nerve AVN and posterior vagal nerve PVN, respectively, of a patient. For example, the distal electrodes 212, 212a can be placed just below the patient's diaphragm. In other embodiments, however, fewer or more electrodes can be placed on or near fewer or more nerves.

In some embodiments the system further comprises an external charger 101 and/or an external programmer 100.

Figure 5:
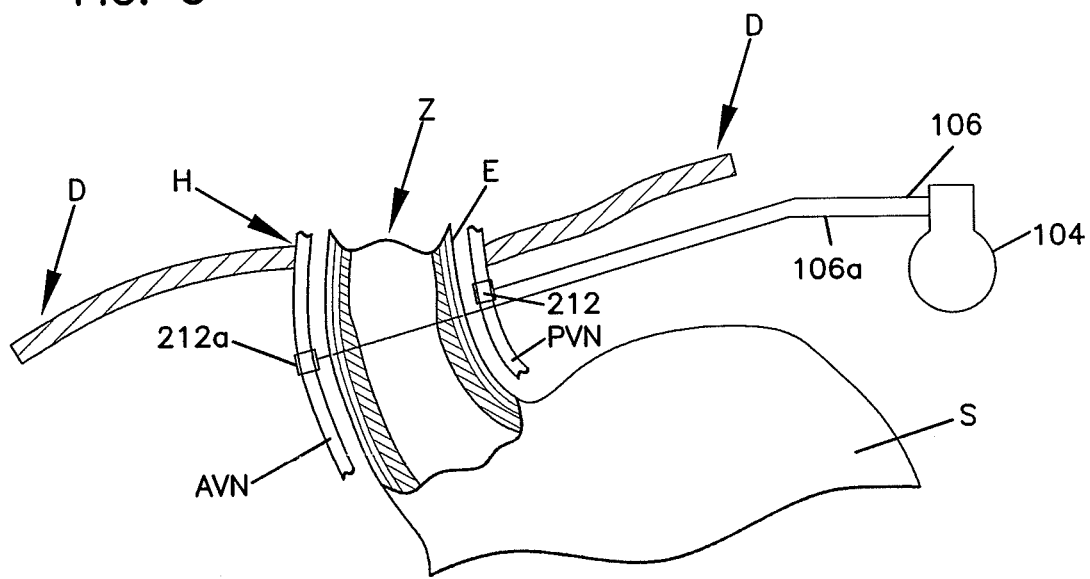
FIG. 5 illustrates a neuroregulator, leads and placement of anterior and posterior electrodes on the vagus nerve.

Another embodiment of a system useful in treating a gastrointestinal disorder or a condition associated with excess weight as described herein is also shown in FIG. 5.

Figure 4:
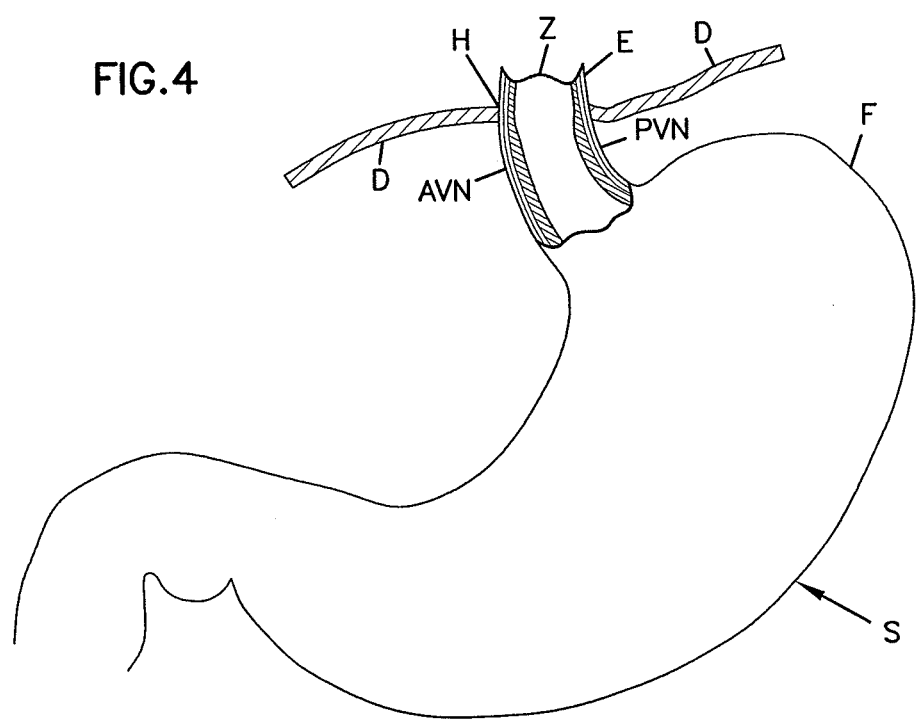
FIG. 4 is a schematic representation of a patient's stomach shown partially in section and illustrating a representative placement of anterior and posterior vagus nerves with respect to the anatomy of the stomach and diaphragm.

With reference to FIG. 4, a stomach S is shown schematically for the purpose of facilitating an understanding of applying a vagal nerve modulating signal. In FIG. 4, the stomach S is shown with a collapsed fundus F which is deflated due to fasting. In practice, the fundus F can be reduced in size and volume (as shown in FIG. 4) or expanded. The esophagus E passes through the diaphragm D at an opening or hiatus H. In the region where the esophagus E passes through the diaphragm D, trunks of the vagal nerve (illustrated as the anterior vagus nerve AVN and posterior vagus nerve PVN) are disposed on opposite sides of the esophagus E. It will be appreciated that the precise location of the anterior and posterior vagus nerves AVN, PVN relative to one another and to the esophagus E are subject to a wide degree of variation within a patient population. However, for most patients, the anterior and posterior vagus nerves AVN, PVN are in close proximity to the esophagus E at the hiatus H where the esophagus E passes through the diaphragm D.

The anterior and posterior vagus nerves AVN, PVN divide into a plurality of trunks that innervate the stomach directly and via the enteric nervous system and may include portions of the nerves which may proceed to other organs such as the pancreas, gallbladder and intestines. Commonly, the anterior and posterior vagus nerves AVN, PVN are still in close proximity to the esophagus E and stomach (and not yet extensively branched out) at the region of the junction of the esophagus E and stomach S.

In the region of the hiatus H, there is a transition from esophageal tissue to gastric tissue. This region is referred to as the Z-line (labeled "Z" in the Figures). Above the Z-line, the tissue of the esophagus is thin and fragile. Below the Z-line, the tissue of the esophagus E and stomach S are substantially thickened and more vascular. Within a patient population, the Z-line is in the general region of the lower esophageal sphincter. This location may be slightly above, slightly below or at the location of the hiatus H.

With reference to FIG. 5, electrodes 212, 212a are shown placed near the esophagus E or proximal portion of the stomach below the diaphragm D and on the anterior and posterior vagus nerves AVN, PVN. In a preferred embodiment, the nerves AVN, PVN are indirectly stimulated by passing electrical signals through the tissue surrounding the nerves. In some embodiments, the electrodes are bipolar pairs (i.e. alternating anode and cathode electrodes). In some embodiments, a plurality of electrodes may be placed overlying the anterior and/or posterior vagus nerves AVN, PVN. As a result, energizing the plurality of electrodes will result in application of a signal to the anterior and posterior vagus nerves AVN, PVN and/or their branches. Of course, only a single array of electrodes could be used with all electrodes connected to an neuroregulator.

The electrical connection of the electrodes to a neuroregulator may be as previously described by having leads (e.g. 106,106a) connecting the electrodes directly to an implantable neuroregulator (e.g. 104). Alternatively, and as previously described, electrodes may be connected to an implanted antenna for receiving a signal to energize the electrodes.

1) Neuroregulator

The neuroregulator (FIG. 3) generates electrical signals in the form of electrical impulses according to a programmed regimen. The neuroregulator utilizes a microprocessor and other standard electrical and electronic components, and in some embodiments, communicates with an external programmer and/or monitor by asynchronous serial communication for controlling or indicating states of the device. Passwords, handshakes and parity checks are employed for data integrity. In some embodiments, the neuroregulator also includes means for conserving energy, which is important in any battery operated device and especially so where the device is implanted for medical treatment of a disorder, and means for providing various safety functions such as preventing accidental reset of the device.

In some embodiments, the neuroregulator 104 initiates the generation and transmission of therapy signals to the lead assemblies 106, 106a. In an embodiment, the neuroregulator 104 initiates therapy when powered by the internal battery 150. In an embodiment, the battery is a secondary (rechargeable) battery or a primary (non-rechargeable) battery. In other embodiments, however, the external mobile charger 101 triggers the neuroregulator 104 to begin generating therapy signals. After receiving initiation signals from the external charger 101, the neuroregulator 104 generates the therapy signals and transmits the therapy signals to the lead assemblies 106, 106a.

Having been programmed by signals from the external mobile charger 101, the neuroregulator 104 generates high and/or low frequency signals to the leads 106, 106a. As will be described, the external mobile charger 101 may have additional functions in that it may provide for periodic recharging of batteries within the neuroregulator 104, and also allow record keeping and monitoring.

While an implantable (rechargeable) power source for the neuroregulator 104 is preferred, an alternative design could utilize an external source of power, the power being transmitted to an implanted module via the RF link (i.e., between coils 102, 105). In this alternative configuration, while powered externally, the source of the specific signals could originate either in the external power source unit, or in the implanted module.

The intermittent aspect of the therapy signal resides in applying the signal according to a prescribed duty cycle. The pulse signal is programmed to have a predetermined on-time in which a train or series of electrical pulses of preset parameters is applied to the vagus branches, followed by a predetermined off-time. Nevertheless, continuous application of the electrical pulse signal may also be effective.

The neuroregulator 104 also may include memory in which treatment instructions and/or patient data can be stored. For example, the neuroregulator 104 can store therapy programs indicating what therapy should be delivered to the patient. The neuroregulator 104 also can store patient data indicating how the patient utilized the therapy system, reacted to the delivered therapy, health profile of the patient, and dosages and/or side effects of agents that treat the gastrointestinal condition or conditions associated with excess weight.

Signals can be applied at a portion of the nervous system remote from the vagus nerve such as at or near the stomach wall, for indirect regulation of the vagus nerve in the vicinity of the sub-diaphragmatic location. Here, at least one neuroregulator is implanted together with one or more electrodes subsequently operatively coupled to the neuroregulator via leads for generating and applying the electrical signal internally to a portion of the patient's nervous system to provide indirect modulation or down regulation of the vagus nerve in the vicinity of the desired location. Alternatively, the electrical signal may be applied non-invasively to a portion of the patient's nervous system for indirect application of the vagus nerve at a sub-diaphragmatic location.

Features may be incorporated into the neuroregulator for purposes of the safety and comfort of the patient. In some embodiments, the patient's comfort would be enhanced by ramping the application of the signal up during the first two seconds. The device may also have a clamping circuit to limit the maximum voltage (30 volts for example) deliverable to the vagus nerve, to prevent nerve damage. An additional safety function may be provided by implementing the device to cease signal application in response to manual deactivation through techniques and means similar to those described above for manual activation. In this way, the patient may interrupt the signal application if for any reason it suddenly becomes intolerable.

The neuroregulator may be programmed with an external programmer such as a programming wand and a personal computer using suitable programming software developed according to the programming needs and signal parameters which have been described herein. The intention, of course, is to permit noninvasive communication with the electronics package after the latter is implanted, for both monitoring and programming functions. Beyond the essential functions, the programming software should be structured to provide straightforward, menu-driven operation, HELP functions, prompts, and messages to facilitate simple and rapid programming while keeping the user fully informed of everything occurring at each step of a sequence. Programming capabilities should include capability to modify the electronics package's adjustable parameters, to test device diagnostics, and to store and retrieve telemetered data. It is desirable that when the implanted unit is interrogated, the present state of the adjustable parameters is displayed on the PC monitor so that the programmer may then conveniently change any or all of those parameters at the same time; and, if a particular parameter is selected for change, all permissible values for that parameter are displayed so that the programmer may select an appropriate desired value for entry into the neuroregulator.

Other desirable features of appropriate software and related electronics would include the capability to store and retrieve historical data, including patient code, device serial number, number of hours of battery operation, number of hours of output, and number of magnetic activations (indicating patient intercession) for display on a screen with information showing date and time of the last one or more activations.

Diagnostic testing should be implemented to verify proper operation of the device, and to indicate the existence of problems such as with communication, the battery, or the lead/electrode impedance. A low battery reading, for example, would be indicative of imminent end of life of the battery and need for implantation of a new device. However, battery life should considerably exceed that of other implantable medical devices, such as cardiac pacemakers, because of the relatively less frequent need for activation of the pulse generator of the present invention. In any event, the nerve electrodes are capable of indefinite use absent indication of a problem with them observed on the diagnostics testing.

The device may utilize circadian or other programming as well, so that activation occurs automatically at normal mealtimes for this patient. This may be in addition to the provision for the manual, periodic between meal, and sensing-triggered activation as described above herein. Another form of treatment may be implemented by programming the neuroregulator to periodically deliver the vagal activity modulation at programmed intervals between prescribed normal mealtimes. This will tend to reduce excessive snacking between meals, which may otherwise be of insufficient quantity within a preset time interval to trigger automatic delivery of the therapy. For bulimic, obese, or compulsive overeating patients, the device can be programmed so that when triggered, vagal activity is modulated and the patient's appetite is suppressed by a feeling of fullness (satiety). In some embodiments, manual activation by the patient is desirable, but because the psychological pattern is difficult to control, the use of circadian programming and detection of overeating by measuring quantity of food consumed during a given interval serves as an important backup in the therapeutic modality.

As discussed above, the neuroregulator may also be activated manually by the patient by any of various means by appropriate implementation of the device. These techniques include the patient's use of an external magnet, or of an external RF signal generator, or tapping on the surface overlying the neuroregulator, to activate the neuroregulator and thereby cause the application of the desired modulating signal to the electrodes. Upon experiencing the compulsive craving, the overweight, obese or bulimic patient can simply voluntarily activate the neuroregulator. If the patient fails to act, the automatic detection of the overeating and consequent application of the necessary therapy will take place through modulation of vagal activity to produce the sensation of satiety.

Neuroregulators, one supplying the right vagus and the other the left vagus may be used. Use of implanted neuroregulators for performing methods as described herein is preferred, but treatment may conceivably be administered using external equipment on an outpatient basis, albeit only somewhat less confining than complete hospitalization. Implantation of one or more neuroregulators, of course, allows the patient to be completely ambulatory, so that normal daily routine activities including on the job performance is unaffected.

2) External Mobile Charger

The optional external charger 101 includes circuitry for communicating with the implanted neuroregulator 104. See FIG. 3. In general, the communication is transmitted across the skin 103 along a two-way signal path as indicated by arrows A. Example communication signals transmitted between the external charger 101 and the neuroregulator 104 include treatment instructions, patient data, and other signals as will be described herein. Energy also can be transmitted from the external charger 101 to the neuroregulator 104 as will be described herein.

In the example shown, the external charger 101 can communicate with the implanted neuroregulator 104 via bidirectional telemetry (e.g. via radiofrequency (RF) signals). The external charger 101 shown in FIG. 3 includes a coil 102, which can send and receive RF signals. A similar coil 105 can be implanted within the patient and coupled to the neuroregulator 104. In an embodiment, the coil 105 is integral with the neuroregulator 104. The coil 105 serves to receive and transmit signals from and to the coil 102 of the external charger 101.

In an embodiment, the external charger 101 can be configured to provide for periodic recharging of the internal power source 150 of the neuroregulator 104. In an alternative embodiment, however, the neuroregulator 104 can entirely depend upon power received from an external source. For example, the external charger 101 can transmit power to the neuroregulator 104 via the RF link (e.g., between coils 102, 105).

The circuitry 170 of the external component mobile charger 101 can be connected to a first external antenna 102. The antenna 102 communicates with a similar antenna 105 implanted within the patient and connected to the neuroregulator 104. The external component is configured to send the therapy instructions to the implantable neuroregulator via the external antenna and the implanted antenna, Communication between the external component mobile charger 101 and the neuroregulator 104 includes transmission of therapy cycle parameters and other signals as will be described.

In other embodiments, the external charger 101 also can provide the instructions according to which the therapy signals are generated (e.g., pulse-width, amplitude, and other such parameters). In a preferred embodiment, the external charger 101 includes memory in which several predetermined programs/therapy schedules can be stored for transmission to the neuroregulator 104. The external charger 101 also can enable a user to select a program/therapy schedule stored in memory for transmission to the neuroregulator 104. In another embodiment, the external charger 101 can provide treatment instructions with each initiation signal.

In embodiments, the external charger can comprise one or more selectable operating modules. The selectable operating modules comprise: an operating room module that is selectable when the external charger is coupled to the first external antenna, the operating room module being associated with at least a testing operation to test appropriate positioning of the implantable component within the body; a therapy delivery module that is selectable when the external charger is coupled to a second external antenna, the therapy delivery module being associated with therapy signal generation; and a diagnostic module that is selectable when the external charger is coupled to an external programmer, the programming module being configured to transfer a therapy schedule from the external programmer to the implantable component.

3) External Programmer

Figure 3:
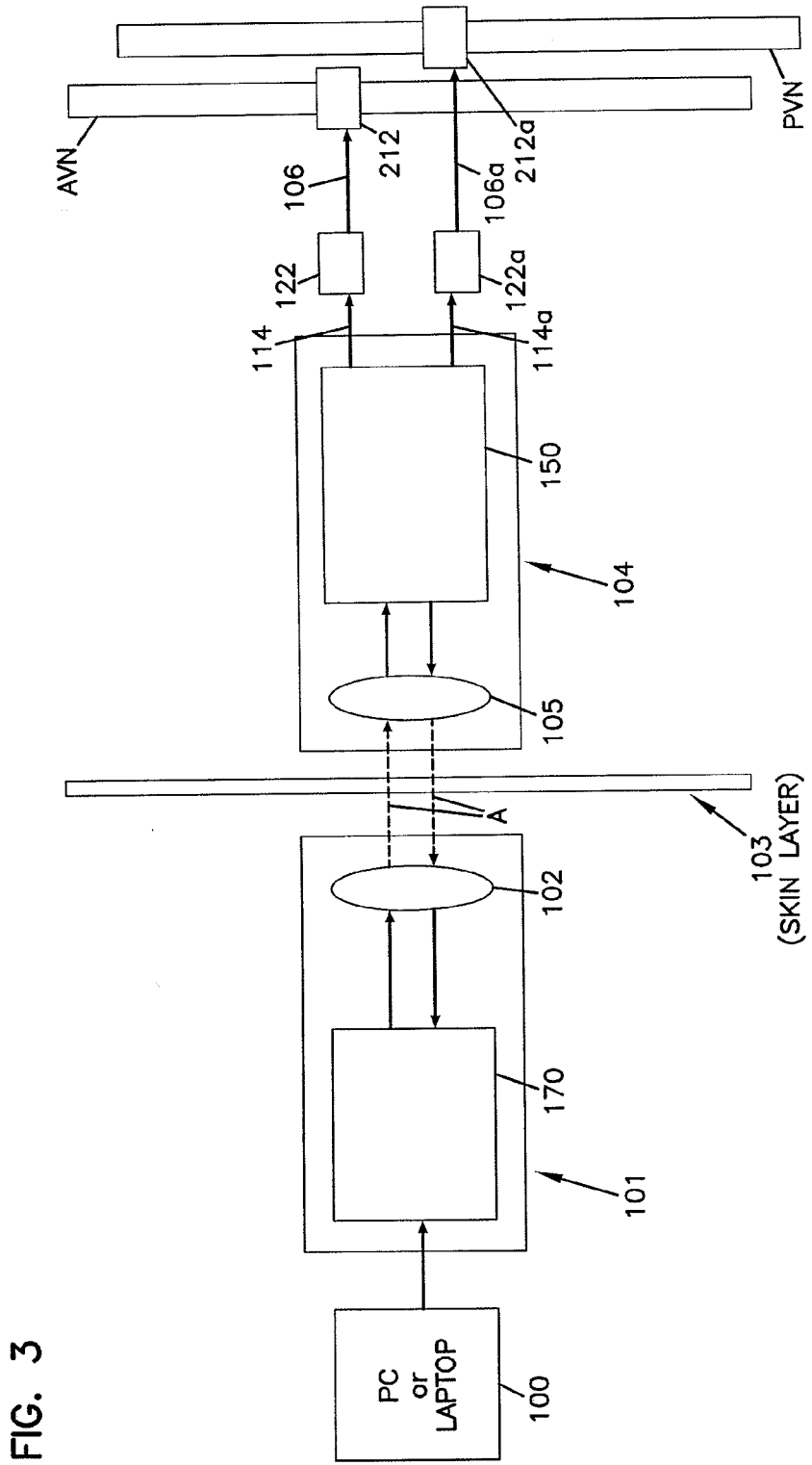
FIG. 3. is a schematic representation of an exemplary implantable system configuration for a gastro-intestinal treatment involving applying an electrical signal to a vagus nerve.

Referring to FIG. 3, in embodiments, a system further optionally comprises an external programmer such as a computer (such as a personal computer) or a mobile device (such as a tablet computer, or cellular phone) 100 that can be connected to the external mobile charger 101. With such a connection, a physician can use the programmer 100 to program therapies into the neuroregulator 104 as will be described. In embodiments, the external programmer is configured to provide therapy instructions comprising parameters for each therapy cycle to the external component. In some embodiments, the therapy cycles include parameters that comprise a high frequency therapy signal and a low frequency therapy signal, an on time period and off time period, the off time period selected to allow at least partial recovery of neural activity. In embodiments, the external programmer is configured to provide therapy instructions that include multiple therapy cycles per treatment period. The external programmer may also provide for one or more than one treatment periods per day or per week.

In embodiments, the external programmer is configured to obtain patient data, wherein the patient data comprises data obtained from the implantable component and patient data concerning the health profile of the patient. A health profile may include the presence or absence of conditions in a subject selected from the group consisting of weight loss, diabetes, hypertension, cardiac condition, liver disorder, a renal disorder and combinations thereof. A health profile may also include age of the patient, the presence of other implantable devices, and medications taken by the patient. Data concerning dosages and/or side effects of agents that treat the gastrointestinal condition or conditions associated with excess weight may also be obtained and stored on the external programmer. Patient data from the implantable component includes the treatment period of therapy actually delivered to the patient, device therapy data, patient use, and compliance data.

C. Therapy Cycle Parameters

In embodiments, the implantable neuroregulator is configured to deliver one or more therapy cycles. Each therapy cycle includes delivering one or more electrical signals having a set of parameters to a nerve. The electrical signal is delivered to the nerve during an on time. Within that on time, the electrical signal may be delivered as one or more sets of pulses. Each set of pulses can have different parameters such as a different frequency from one another. If an electrical signal is delivered as a set of pulses at a selected frequency, the pulse width of each pulse in the set of pulses is less than the period of the selected frequency. In some embodiments, an electrical signal comprises a set of pulses of two different frequencies. During the on time there may be a delay period between some of the sets of pulses. In embodiments, some of the signals at different frequencies may overlap one another while others are separated from one another by a delay period. In some embodiments, the delay period between pulses is the same regardless of the frequency of the set of pulses. In other embodiments, the delay period between a set of pulses of one frequency differs from that of a set of pulses at another frequency. While the systems and methods are preferably applied to a vagus nerve, such systems and methods could also be applied to other nerves such as the splanchnic, celiac, and other cranial nerves.

In embodiments, the therapy cycle comprises an electrical signal comprising a set of pulses applied at a first selected frequency of about 150-10,000 Hz, wherein each pulse of the set of pulses has a pulse width of at least 0.01 milliseconds and less than the period of the first selected frequency. The period of the selected frequency is the reciprocal of the frequency in seconds. For example, the period of signal at a frequency of 1000 Hz for a pulse is the reciprocal of the frequency in seconds; 1 millisecond. During the on time, the set of pulses can be applied once or a number of times depending on the desired amount of total charge delivered during the therapy cycle. In embodiments, a therapy cycle delivers about 0.2 coulombs or less of charge. In embodiments, when more than one set of pulses are delivered during an on time at least some of the sets of pulses are separated by a delay period. The delay period can be the same between set of pulses or it can be different.

The first selected frequency can range from about 150 to about 10,000 Hz. In other embodiments, the first selected frequency has a frequency of about 150 to 5000 Hz, preferably about 200 to 5000 Hz, preferably about 250 to 5000 Hz, preferably about 500 to 5000 Hz or preferably about 1000 to 5000 Hz. In an embodiment, the first selected frequency is about 1000 Hz or greater, and has a pulse width of about 0.01 milliseconds to about 0.09 milliseconds. In embodiments, the electrical signal is applied at a frequency that at least partially downregulates activity on the nerve.

In embodiments, the set of pulses have a current amplitude of about 0.1 to 20 mAmps, preferably about 0.1 to 15 mAmps, preferably about 0.1 to 10 mAmps, preferably about 0.1 to 5 mAmps, preferably about 6 to 20 mAmps, preferably about 10 to 20 mAmps, or preferably about 10 to 16 mAmps.

In embodiments, the pulse width of each pulse is about 0.01 milliseconds to about 6 milliseconds, preferably about 0.01 to 4 milliseconds, preferably about 0.01 to 2 milliseconds, preferably about 0.01 to 1 millisecond, preferably about 0.01 to 0.2 milliseconds, or preferably about 0.01 to about 0.1 millisecond. While not meant to limit the scope of the disclosure, it is believed that for an electrical signal delivered at a frequency of 150 Hz or greater, a pulse width of less than 0.01 milliseconds is not effective to change the activity of the nerve. As discussed above, in embodiments, the parameters of the electrical signal at least partially downregulate activity on the nerve.

In embodiments, the pulses in a set of pulses can be monophasic or biphasic or a mixture of monophasic and biphasic. In embodiments, some pulses can be monophasic, in which the pulse width is the simple width of the pulse. In embodiments, some pulses can be biphasic, or comprise more complex waveforms. In these cases, the pulse width is the width of the waveform from beginning to end. The period is the reciprocal of the frequency.

In embodiments, the set of pulses at the first selected frequency can be delivered once or more than once during the on time. If a set of pulses is delivered more than once during the on time, the set of pulses are referred to as a burst of signal. In embodiments, there may be a delay period between the sets of pulses. The delay period between each burst may be the same or different. In an embodiment, more than one burst of pulses having a frequency of at least 150 Hz are delivered during an on time. Each burst lasts at least about 26 milliseconds, and each burst is separated by a delay period of at least about 0.3 seconds.

In embodiments, the therapy cycle is a low charge therapy cycle delivering a total charge of 0.2 coulombs or less to the nerve. In embodiments, the total amount of charged delivered in a therapy cycle is about 5 microcoulombs to about 100,000 microcoulombs, more preferably about 10 microcoulombs to about 50,000 microcoulombs, more preferably about 10 microcoulombs to about 10,000 microcoulombs, or more preferably about 10 microcoulombs to about 1000 microcoulombs. In embodiments, the therapy cycle comprising at least one set of pulses having a frequency of at least 150 Hz delivers about 5 microcoulombs of charge or greater. While not meant to limit the scope of the disclosure, it is believed that a low charge therapy cycle as described herein provides for at least partial downregulation of nerve activity while conserving the energy required to power the therapy cycle. In embodiments, the amount of required energy is decreased so that a primary battery rather than a rechargeable battery may be employed in the systems described herein.

In embodiments, the electrical signal that further comprises: a) a set of pulses applied at a second selected frequency of about 1-10,000 Hz, wherein each pulse of the set of pulses has a pulse width of at least 0.05 microseconds and less than the period of the second selected frequency. In embodiments, the second selected frequency is different than the first selected frequency.

The second selected frequency can range from about 1 to about 10,000 Hz. In other embodiments, the second selected frequency has a frequency of about 1 to 1000 Hz, preferably about 1 to 200 Hz, preferably about 1 to 150 Hz, preferably about 1 to 50 Hz, or preferably about 1 to 10 Hz. In an embodiment, the second selected frequency is about 40 Hz or greater, and has a pulse width of about 0.05 microseconds or greater.

In embodiments, the pulse or set of pulses have a current amplitude of about 0.1 to 20 mAmps, preferably about 0.1 to 15 mAmps, preferably about 0.1 to 10 mAmps, preferably about 0.1 to 5 mAmps, preferably about 0.1 to 1 mAmp, preferably about 6 to 20 mAmps, preferably about 10 to 20 mAmps, or preferably about 10 to 16 mAmps.

In embodiments, the pulse width of each pulse is about 0.05 microseconds to about 0.5 second, preferably about 0.1 microseconds to about 0.1 seconds, preferably about 0.5 microseconds to about 0.05 seconds, or preferably about 1 microsecond to 0.006 seconds.

In embodiments, the pulses in a set of pulses can be monophasic or biphasic or a mixture of monophasic and biphasic. In embodiments, some pulses can be monophasic, in which the pulse width is the simple width of the pulse. In embodiments, some pulses can be biphasic, or comprise more complex waveforms. In these cases, the pulse width is the width of the waveform from beginning to end. The period is the reciprocal of the frequency. If a biphasic pulse is employed the pulse width is the width of the up and down swing, and this sum is less than the period.

In embodiments, the set of pulses at the second selected frequency can be delivered once or more than once during the on time. If a set of pulses is delivered more than once during the on time, the set of pulses are referred to as a burst of signal. In embodiments, there may be a delay period between the sets of pulses. The delay period between each burst may be the same or different. In an embodiment, more than one burst of pulses having a frequency of at less than 150 Hz are delivered during an on time. In embodiments, each burst has about 1 to about 20 pulses, and lasts at least about 10 microseconds, and each burst is separated by a delay period of at least 2.5 milliseconds.

In embodiments, the therapy cycle is a low charge therapy cycle delivering a total charge of 0.2 coulombs or less to the nerve. In embodiments, the total amount of charge delivered in a therapy cycle is about 5 microcoulombs to about 100,000 microcoulombs, more preferably about 10 microcoulombs to about 50,000 microcoulombs, more preferably about 10 microcoulombs to about 10,000 microcoulombs, or more preferably about 10 microcoulombs to about 1000 microcoulombs. In embodiments, the therapy cycle comprising at least one set of pulses having a frequency of less than 150 Hz delivers about 5 microcoulombs of charge or greater.

In embodiments, the set of pulses applied at a first selected frequency of 150 Hz or greater is followed by the set of pulses applied at a second selected frequency of about 1-10,000 Hz. In embodiments, the set of pulses applied at a first selected frequency of 150 Hz or greater is followed by the set of pulses applied at a second selected frequency of about 1-150 Hz. In other embodiments, the set of pulses applied at a second selected frequency of about 1-10,000 Hz is followed by the set of pulses applied at a first selected frequency of 150 Hz or greater. In yet other embodiments, one or more of the set of pulses may be applied simultaneously or overlapping one another.

In embodiments, an on time of the therapy cycle is at least 30 seconds, more preferably about 30 seconds to 30 minutes, 30 seconds to 20 minutes, 30 seconds to 10 minutes, 30 seconds to 5 minutes, 30 seconds to 2 minutes, and 30 seconds to 1 minute. In embodiments, the therapy cycle has an offtime during which no signal is delivered. In embodiments, the time of the off time is selected to allow at least partial recovery of nerve activity. In embodiments the offtime is at least 30 seconds, more preferably 30 seconds to 30 minutes, 30 seconds to 20 minutes, 30 seconds to 10 minutes, 30 seconds to 5 minutes, 30 seconds to 2 minutes, and 30 seconds to 1 minute. A therapy cycle can comprises one or more on times and one or more offtimes. In an embodiment, the therapy cycle includes 2 minutes of on time, 1 minute of off time, 2 minutes of on time, and 5 minutes of off time. While not meant to limit the scope of the inventive subject matter, it is believed that electrical signals that are delivered with an on time and an off time minimize gastric accommodation, decrease discomfort for the patient, and minimize damage to the nerve.

In embodiments, the neuroregulator is configured to deliver one or more than one therapy cycle in a treatment period. A treatment period ranges from about 6 to 24 hours, preferably 6 to 18 hours, 6 to 12 hours, and 6 to 9 hours. In an embodiment, a treatment period is at least 6 hours.

Figure 6A:
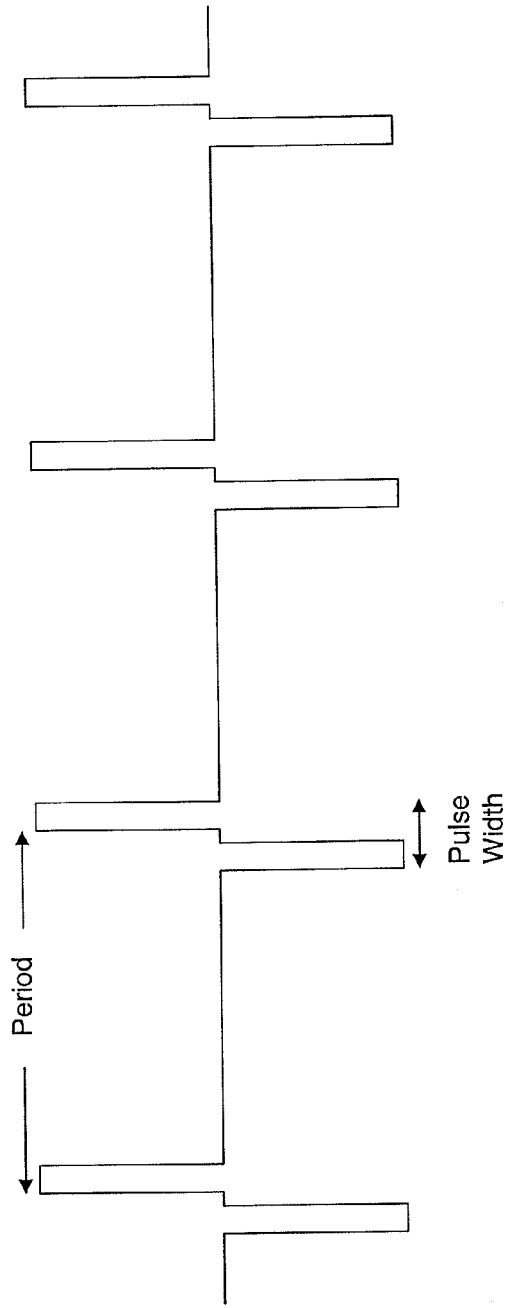
FIG. 6a-c illustrate examples of a therapy cycle delivered to the vagus nerve. a) shows a therapy cycle with an electrical signal having a frequency of about 150 to 10,000 Hz with a pulse width of at least 0.01 milliseconds and less than the period of the selected frequency; b) shows a therapy cycle with an electrical signal having a first selected frequency of about 150 to 10,000 Hz with a pulse width of at least 0.01 milliseconds and less than the period of the selected frequency followed by an electrical signal having a second selected frequency of about 1 to 150 Hz with a pulse width of at least about 0.05 microseconds but less than the period of the second selected frequency; and c) shows a therapy cycle with an electrical signal having a frequency of about 150 to 10,000 Hz with a pulse width of at least 0.01 milliseconds and less than the period of the selected frequency applied in a series of short bursts with a delay period between each burst.
Figure 6B:
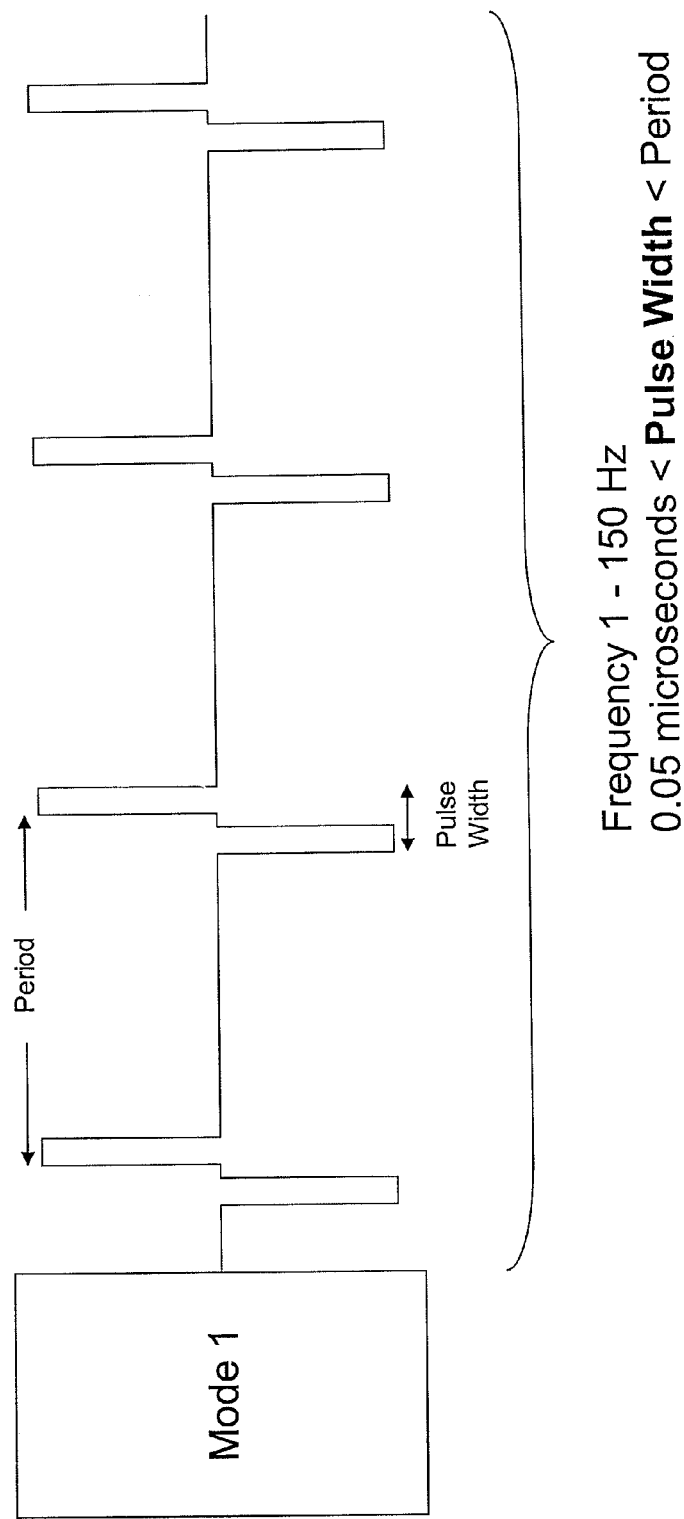

Exemplary therapy cycles are illustrated in FIGS. 6 a-c. In FIG. 6a, the therapy cycle comprises an electrical signal comprising a set of pulses that has a frequency of about 150 to 10,000 Hz, and a pulse width of at least 0.01 milliseconds but less than the period for the selected frequency. In embodiments the electrical signal is a biphasic signal of 1000 Hz or greater with a pulse width of 90 microseconds or greater. While not meant to limit the disclosure, it is believed that a set of pulses that do not fill the entire period can be delivered to the nerve and provide for at least partial downregulation of the activity on the nerve and conserve energy, especially when high frequency signals are delivered to the nerve In FIG. 6b, the therapy cycle comprises an electrical signal comprising a set of pulses that has a frequency of about 150 to 10,000 Hz, and a pulse width of at least 0.01 milliseconds but less than the period for the selected frequency followed by a signal having a second selected frequency of about 1 to 150 Hz with a pulse width of at least 0.05 microseconds but less than the period of the second selected frequency. In embodiments the electrical signal is a biphasic signal of 1000 Hz or greater with a pulse width of 90 microseconds or greater and the signal of the second selected frequency is a biphasic pulse at a frequency of at least 40 Hz with a pulse width of at least 0.05 microseconds.

Figure 6C:
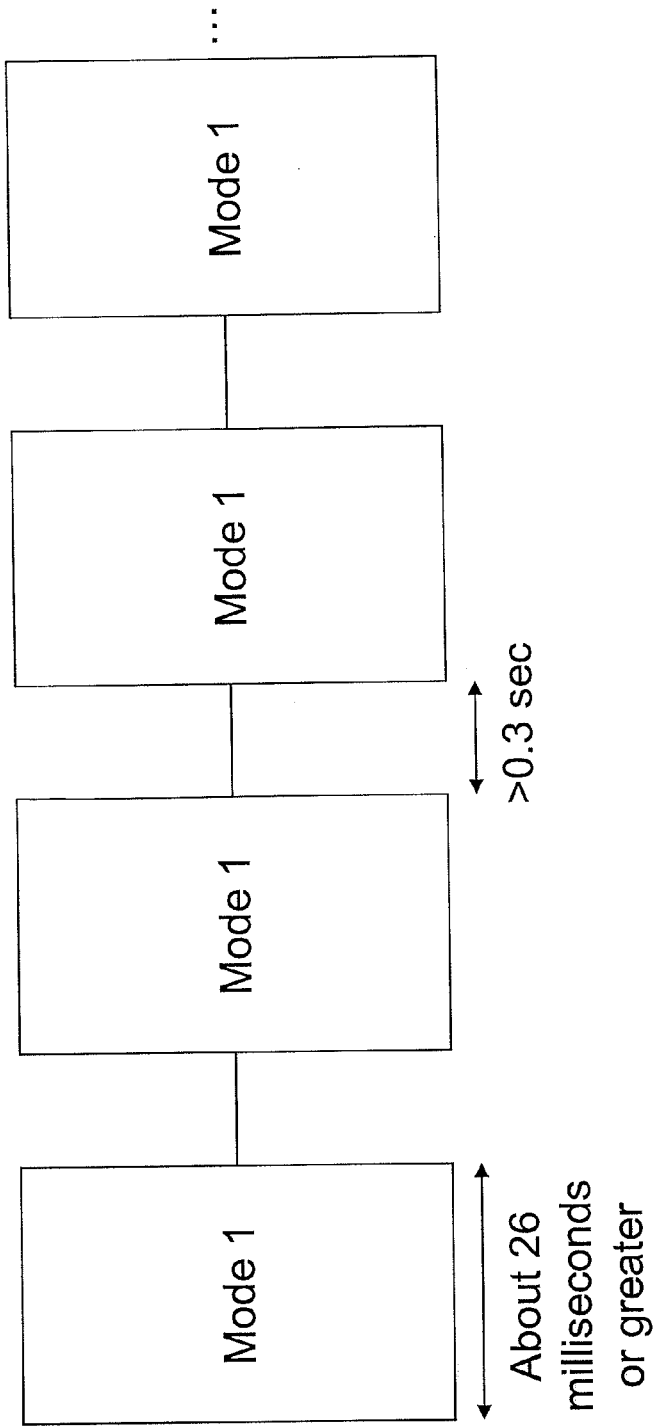

In FIG. 6c, the therapy cycle comprises an electrical signal comprising a plurality of a set of pulses that have a frequency of about 150 to 10,000 Hz, and a pulse width of at least 0.01 milliseconds but less than the period for the selected frequency. Each set of pulses is delivered in about 26 milliseconds or greater with a delay period between each set of pulse of 0.3 seconds or greater. The therapy cycle illustrated in this figure shows bursts of signal followed by a delay period.

In embodiments, the therapy cycle comprises an electrical signal comprising: a) a set of pulses that have a frequency of about 150 Hz or greater; and b) a total amount of charge delivered to the nerve of about 5 microcoulombs to about 200,000 microcoulombs during the therapy cycle. While not meant to limit the scope of the invention, it is believed that delivering a low amount of charge during a therapy cycle provides effective treatment while saving energy. In embodiments, the electrical signal is applied at a frequency that at least partially downregulates activity on the nerve.

The total amount of charge delivered during the on time of the therapy cycle can be determined based on the pulse width, current amplitude, frequency and total on time of the signal and are related by the following equation:

Total charge per cycle=(current amplitude)×(pulse width)×(frequency)×(cycle time)

For a biphasic pulse this equation is divided by 2. In embodiments, the total amount of charge delivered in a therapy cycle is about 10 microcoulombs to about 200,000 microcoulombs, more preferably about 10 microcoulombs to about 100,000 microcoulombs, more preferably about 10 microcoulombs to about 50,000 microcoulombs, more preferably about 10 microcoulombs to about 10,000 microcoulombs, or more preferably about 10 microcoulombs to about 1000 microcoulombs.

In some embodiments, a therapy cycle further comprises one or more electrical signals having a second selected frequency of less than 150 Hz, and an on time of at least 30 seconds. In embodiments, the frequency of about 150 Hz or greater is different than the second selected frequency. During the on time, both the frequency of about 150 Hz or greater and the second selected frequency signals are delivered to the nerve. In embodiments, the signal having a frequency of about 150 Hz or greater is referred to as a high frequency signal and the second selected frequency signal is referred to as a low frequency signal.

In some embodiments, the frequency of about 150 Hz or greater of the electrical signal ranges from about 150 to 10,000 Hz, about 200 to 8000 Hz, or about 250 to 5000 Hz. In some embodiments, the frequency of about 150 Hz or greater of the electrical signal is about 500 to 1000 Hz. In some embodiments, one or more second selected frequency electrical signal is about 0.5 to 199 Hz, 1 to 150 Hz, or 10 to 100 Hz. In some embodiments, the second selected frequency of the electrical signal is about 10 to 50 Hz. In some embodiments, additional signals at the low frequency will be numbered numerically, e.g., third selected signal, fourth selected signal, etc. While not meant to limit the scope of the disclosure, it is believed that the combination of the high frequency signal and a low frequency signal provides at least a partial downregulation of activity on the nerve.

In embodiments, a signal having a frequency of about 150 Hz or greater comprises a frequency of 200 Hz or greater and include a plurality of charge pulses with pulse widths of about 0.06 to 3000 milliseconds, about 25 to 300 milliseconds, or about 0.06 to 100 milliseconds. In embodiments, a second selected frequency electrical signal can include a plurality of charge pulses with pulse widths of about 0.025 to 25 microseconds or about 0.05 to about 0.5 microseconds. In embodiments, the low frequency signal comprises packets of 1 to 20 pulses, each pulse having a pulse width of 500 nanoseconds or less.

In embodiments, a signal having a frequency of about 150 Hz or greater can comprise a frequency of 200 Hz or greater and have a current amplitude of about 1 to 20 mA, about 1 to 6 mA, or about 1 to 3 mA. In embodiments, a signal having a frequency of about 150 Hz or greater comprises a frequency of 200 Hz or greater, pulse widths of 60 microseconds or greater.

In embodiments, a second selected frequency signal has a frequency of less than 200 Hz and has a current amplitude of 1 mA or less. In embodiments, a second selected frequency signal comprises a frequency of less than 200 Hz, and a pulse width of about 100 to 500 nanoseconds. In embodiments, a third selected frequency signal comprises a frequency of less than 200 Hz, and a pulse width of 50 to 500 nanoseconds. In embodiments, each signal comprises about 1 to 20 pulses.

In embodiments, the voltage of each signal can vary. In embodiments of the signal having a frequency of about 150 Hz or greater, the voltage is about 1 to 24 volts. In embodiments, the second selected frequency signal has a voltage of about 1 to 15 volts, or 5 to 15 volts. In embodiments, the second selected frequency signal has a voltage of about 0.1 to about 2 volts, or 0.2 volts to 1 volt.

In embodiments, a therapy cycle comprises one or more additional selected frequency electrical signals that are delivered simultaneously, precede, follow, or precede and follow a signal having a frequency of about 150 Hz or greater. In embodiments, a second selected frequency signal, a third selected frequency signal, and a signal having a frequency of about 150 Hz or greater can be delivered simultaneously during an on time of the therapy cycle, each signal having at least one parameter that differs from the other signals. In embodiments, the second selected frequency signal can be applied first followed by the signal having a frequency of about 150 Hz or greater followed by the third selected frequency signal during an on time. In an embodiment, the second and third selected frequency signals are initiated and applied throughout the on time and a signal having a frequency of about 150 Hz or greater is delivered after the initiation of the second and third selected frequency signals. In an embodiment, a third selected frequency signal can be applied first and overlap with a signal having a frequency of about 150 Hz or greater, and then the second selected frequency signal continues in concert with the third selected frequency signal during the on time. In an embodiment, a second selected frequency signal can be applied first and overlap with a signal having a frequency of about 150 Hz or greater, and then the third selected frequency signal is applied during the on time. In embodiments, the second and third selected frequency signals are applied throughout the on time and the high frequency signal is delivered once during the on time.

In embodiments, an on time for therapy cycle can range from 1 second to 30 minutes or more, 30 seconds to 5 minutes, from 30 seconds to 10 minutes, or from 1 second to 2 minutes. The on time can optionally include a ramp up and a ramp down time of about 2 to 60 seconds. The off times of the electrical signal in the therapy cycle are selected to allow for at least partial recovery of nerve activity. In embodiments, the off times can be selected from about 30 seconds to about 20 minutes, 1 minute to 10 minutes, or 1 minute to 5 minutes.

The implantable component may be configured to generate therapy cycles for a treatment period. The therapy cycles can be continuous or intermittent. In some cases, the treatment period is at least 6 hours. In embodiments, a treatment period is from 30 minutes to 24 hours, 30 minutes to about 12 hours, 30 minutes to 9 hours, 30 minutes to 8 hours, or 30 minutes to 6 hours. In embodiments, a therapy cycle comprises 30 minutes of continuous electrical signal treatment on time with no off times. In some embodiments, treatment periods may be related to the period of time before and after eating of a meal.

D. Methods

The disclosure provides a method for manufacturing a system comprising: providing at least one electrode configured to be implanted and placed at a vagus nerve, the electrode is also configured to apply therapy to the vagus nerve upon application of a therapy cycle to the electrode; providing an implantable component for placement in the body of the patient beneath the skin layer, the implantable component being coupled to an implanted antenna and the electrode, and configuring the implantable component to generate a therapy cycle and to transmit the therapy cycle to the electrode. In other embodiments the method further comprises providing an external charger to be placed above the skin layer and adapted to communicate with the implanted antenna across the skin layer through radiofrequency communication. In some embodiments, the external charger includes a plurality of selectable operating modules, each operating module being associated with a different set of operations available for selection by a user. In embodiments, the method further comprises configuring the external charger to couple to a first external antenna and to send the therapy instructions to the implantable component via the first external antenna and the implanted antenna; providing an external programmer and configuring the external programmer to a) communicatively couple to the external charger via a second port, b) to provide therapy instructions comprising parameters for each therapy cycle to the external component. In embodiments, the therapy cycle parameters are as described herein in Section C. In an embodiment, the parameters comprise a high frequency and a low frequency signal, the electrical signals having an on time period and off time period, the off time period selected to allow partial recovery of nerve function.

In other embodiments, the disclosure provides a method of selecting parameters for a therapy cycle for an implantable device in a subject comprising: selecting parameters of a therapy cycle to be applied to a vagus nerve, wherein the therapy cycle comprises an electrical signal comprising i)) a set of pulses applied at a first selected frequency of about 150-10,000 Hz, wherein each pulse of the set of pulses has a pulse width of at least 0.01 milliseconds and less than the period of the first selected frequency; b) communicating the selected parameters to the implantable device comprising the system of claim 1; and c) determining the amount of actual therapy delivered over a time period and adjusting the length of the treatment period to achieve delivery of at least 6 hours of treatment or adjusting the parameters of the therapy cycle or the length of the treatment period or both to increase the amount of excess weight loss, to affect the blood pressure, and/or diabetes of the subject.

In embodiments, the method further comprises selecting the parameters of an electrical signal that comprises: a) a set of pulses applied at a second selected frequency of about 1-10,000 Hz, wherein each pulse of the set of pulses has a pulse width of at least 0.05 microseconds and less than the period of the second selected frequency.

Any of the parameters as described above for the electrical signal of a first selected frequency and a second selected frequency apply to these methods, and can be selected and modified as necessary to increase the amount of excess weight loss, to affect blood pressure, and/or diabetes.

The term "excess weight loss" (EWL) as used herein is determined as follows: ideal body weight is calculated by measuring each subject's height and then determining the body weight that would result in a BMI of 25.0 for that subject, i.e., ideal body weight (kg)=25×height$^2$ (m). EWL is calculated by dividing weight loss by excess body weight [(total body weight)−(ideal body weight)] and multiplying by 100. Thus, EWL %=(weight loss (kg)/excess body weight (kg))×100.

In embodiments, if the amount of excess weight loss is less than 5%, parameters and/or treatment periods are adjusted to increase excess weight loss to at least 10%. Parameters and/or treatment periods may be adjusted once or more than once in order to reach an excess weight loss of at least 10%. In embodiments, the method further comprises selecting the parameters of the therapy cycle based on the starting body mass index of the subject, such as a body mass index of at least 25 or greater.

In other embodiments, a method of selecting parameters for a therapy cycle for an implantable device in a subject comprising: selecting parameters of a therapy cycle to be applied to a vagus nerve to affect blood pressure and/or diabetes of the subject, wherein the parameters comprise an electrical signal having a first selected frequency of 200 Hz or greater, an electrical signal having a second selected frequency of less than 200 Hz, having an on time of at least 30 seconds, and having an off time that allows at least partial recovery of nerve activity; communicating the selected parameters to the implantable device using the system described above; and determining the amount of actual therapy delivered over a time period and adjusting the treatment period to achieve delivery of at least 6 hours of treatment or adjusting the parameters of the therapy cycle or both to affect the blood pressure and/or diabetes of the subject. is provided.

In a further embodiment, the method further comprises selecting the parameters of the therapy cycle based on the starting blood pressure of the subject, such as a systolic blood pressure of at least 140 mmHg or a diastolic blood pressure of 90 mmHg. In embodiments, if the amount of change in systolic blood pressure is less than 5 mmHg, parameters and/or therapy cycles are adjusted to decrease blood pressure at least 10 mmHg. Parameters and/or therapy cycles may be adjusted once or more than once in order to reach a systolic blood pressure of at least 130 mmHg.

In another embodiment, the method further comprises selecting the parameters of the therapy cycle based on the need to treat diabetes. Patients with Type 2 diabetes have a fasting plasma glucose of 126 mg/dl or greater; oral glucose tolerance of 200 mg/dl or greater; and/or % of HbA1C of 6.5% or greater. In some cases, the HbA1C percentage is 6-7%, 7-8%, 8-9%, 9-10%, and greater than 10%. In embodiments, if the amount of change in % of HbA1C is less than 0.5% parameters and/or therapy cycles are adjusted to decrease % of HbA1C at least 1%. Parameters and/or therapy cycles may be adjusted once or more than once in order to reach a % of HbA1C of at least 7%.

Another aspect of the disclosure provides a method of treating a gastrointestinal disorder or a condition associated with excess weight in a subject comprising: applying an electrode to a vagus nerve at a location below vagal innervation of the heart; applying a therapy cycle to the vagus nerve, wherein each therapy cycle comprises a high frequency electrical signal having a first selected frequency of at least 150 Hz, a low frequency electrical signal having a second selected frequency of less than 150 Hz, an on period of at least 30 seconds, and an off period, wherein the off period is selected to allow at least partial recovery of nerve activity.

Another aspect of the disclosure provides a method of treating a gastrointestinal disorder or a condition associated with excess weight in a subject comprising: applying an electrode to a vagus nerve at a location below vagal innervation of the heart; applying a therapy cycle to the vagus nerve, wherein the therapy cycle comprises an on time during which an electrical signal is delivered, the electrical signal comprising: a) a set of pulses applied at a first selected frequency of about 150-10,000 Hz, wherein each pulse of the set of pulses has a pulse width of at least 0.01 milliseconds and less than the period of the first selected frequency. In embodiments, the methods can involve delivering one or more therapy cycles having a combination of parameters as described herein in section C. In embodiments, the method further comprises a set of pulses applied at a second selected frequency of about 1-10,000 Hz, wherein each pulse of the set of pulses has a pulse width of at least 0.05 microseconds and less than the period of the second selected frequency.

In embodiments, the first selected frequency has a frequency of at least 1000 Hz and the second selected frequency has a frequency of at least 40 Hz. In other embodiments, the low frequency signal precedes the high frequency signal and/or follows the high frequency signal.

Another aspect of the disclosure provides a method of treating a gastrointestinal disorder or a condition associated with excess weight in a subject comprising: applying an electrode to a vagus nerve at a location below vagal innervation of the heart; applying a therapy cycle to the vagus nerve, wherein the therapy cycle comprises an on time during which an electrical signal is delivered, the electrical signal comprising: a) a set of pulses that have a frequency of about 150 Hz or greater; and b) a total amount of charge delivered to the nerve of about 5 microcoulombs to 200,000 microcoulombs during the therapy cycle.

In embodiments of the methods described herein one or more electrical signals are applied to the vagus nerve. A neuroregulator, as described above, is employed to regulate the application of the signals. The characteristics of the signal include frequency of the signal, location of the signal, and the administration cycle of the signal. Signal characteristics are selected to enhance a sensation of satiety, to modulate intestinal motility and rate of digestion, and/or partial restoration of the nerve activity following discontinuance of the signal, and to minimize enteric accommodation. The parameters for the electrical signal include those as described herein in section C.

Recognition of recovery of endogenous vagal activity (and recognition of the significant variability between subjects) permits a treatment therapy and apparatus with enhanced control and enhanced treatment options. It is expected there will be significant patient-to-patient variability. For example, some patients' responses to electrical signals may not be as dramatic as illustrated. Others may experience recovery slopes steeper or shallower than illustrated. Also, vagal activity in some subjects may remain flat at a reduced level before increasing toward baseline activity. Vagal activity can be measured in any number of ways. For example, quantities of pancreatic exocrine secretion produced per unit time are an indirect measurement of such activity or effects on blood pressure can be measured in hypertensive subjects. Also, activity can be measured directly by monitoring electrodes on or near the vagus. Such activity can also be ascertained qualitatively (e.g., by a patient's sensation of bloated feelings or normalcy of gastrointestinal motility).

1) Location of Signal Application

Electrodes can be positioned at a number of different sites and locations on or near the vagus nerve. In some embodiments, the electrode is positioned to apply a signal to a branch or trunk of the vagus nerve. In other embodiments, the electrode is positioned to apply a signal to an anterior trunk, posterior trunk or both. The electrode may also be positioned to apply a signal to an organ in proximity to the vagus nerve such as the esophagus or stomach. In some embodiments, the electrode is positioned to apply an electrical signal to the vagus nerve at a location near or distal to the diaphragm of the subject. In other embodiments, up-regulation, or at least partial down-regulation of other nerves (e.g. the splanchnic, or celiac nerves), may be used, alone, or in combination with up-regulation or at least partial down-regulation of the vagus nerve.

For example, FIG. 2 illustrates placement of an electrode. Referring to FIG. 2, the baseline vagal activity is illustrated by the solid line of the proximal vagus nerve segment VNP. The remainder of the vagus and enteric nervous system are shown in reduced thickness to illustrate down-regulation of tone. The pancreo-biliary output (and resulting feedback) is also reduced. In FIG. 2, the electrode is shown high on the vagus relative to the GI tract innervation (e.g., just below the diaphragm), a sole electrode could be placed lower (e.g., just proximal to pancreo/biliary innervation VN5 ).

In other embodiments, alternative designs for placing electrodes on or near the vagus nerve in a region of the esophagus E either above or below the diaphragm are provided. Two paired electrodes may connect to a pulse generator for bi-polar pacing. In other embodiments, a portion of the vagus nerve VN is dissected away from the esophagus E. An electrode is placed between the nerve VN and the esophagus E. The electrode is placed overlying the vagus nerve VN on a side of the nerve opposite electrode and with electrodes axially aligned (i.e., directly across from one another). Not shown for ease of illustration, the electrodes may be carried on a common carrier (e.g., a PTFE or silicone cuff) surrounding the nerve VN. Other possible placements of electrodes are described herein US 2005/0131485 published Jun. 16, 2005, which patent publication is hereby incorporated by reference.

While any of the foregoing electrodes could be flat metal pads (e.g., platinum), the electrodes can be configured for various purposes. In an embodiment, an electrode is carried on a patch. In other embodiments, the electrode is segmented into two portions both connected to a common lead and both connected to a common patch. A flexible patch permits articulation of the portions of the electrodes to relieve stresses on the nerve VN.

2) Therapy Cycle Parameters

Therapy cycle parameters useful in the methods described herein are described above in section C. Such parameters may be adjusted or modified depending on the needs or progress of the patient with regard to weight loss, diabetes, or hypertension.

In embodiments, the implantable component is configured to deliver one or more therapy cycles. Each therapy cycle includes delivering one or more electrical signals having a set of parameters to a nerve.

In embodiments, the therapy cycle comprises an electrical signal comprising a set of pulses applied at a first selected frequency of about 150-10,000 Hz, wherein each pulse of the set of pulses has a pulse width of at least 0.01 milliseconds and less than the period of the first selected frequency. The period of the selected frequency is the reciprocal of the frequency in seconds. For example, the period of signal at a frequency of 1000 Hz for a pulse is the reciprocal of the frequency in seconds; 1 millisecond. During the on time, the set of pulses can be applied once or a number of times depending on the desired amount of total charge delivered during the therapy cycle. In embodiments, a therapy cycle delivers about 0.2 coulombs or less of charge. In embodiments, when more than one set of pulses are delivered during an on time at least some of the sets of pulses are separated by a delay period. The delay period can be the same between sets of pulses or it can be different.

The first selected frequency can range from about 150 to about 10,000 Hz. In other embodiments, the first selected frequency has a frequency of about 150 to 5000 Hz, preferably about 200 to 5000 Hz, preferably about 250 to 5000 Hz, preferably about 500 to 5000 Hz, or preferably about 1000 to 5000 Hz. In an embodiment, the first selected frequency is about 1000 Hz or greater, and has a pulse width of about 0.01 milliseconds to 0.09 milliseconds. In embodiments, the electrical signal is applied at a frequency that at least partially downregulates activity on the nerve.

In embodiments, the set of pulses have a current amplitude of about 0.1 to 20 mAmps, preferably about 0.1 to 15 mAmps, preferably about 0.1 to 10 mAmps, preferably about 0.1 to 5 mAmps, preferably about 6 to 20 mAmps, preferably about 10 to 20 mAmps, or preferably about 10 to 16 mAmps.

In embodiments, the pulse width of each pulse is about 0.01 milliseconds to about 6 milliseconds, preferably about 0.01 to 4 milliseconds, preferably about 0.01 to 2 milliseconds, preferably about 0.01 to 1 millisecond, preferably about 0.01 to 0.2 milliseconds, or preferably about 0.01 to about 0.1 millisecond. While not meant to limit the scope of the disclosure, it is believed that for an electrical signal delivered at a frequency of 150 Hz or greater, a pulse width of less than 0.01 milliseconds is not effective to change the activity of the nerve. As discussed above, in embodiments, the parameters of the electrical signal at least partially downregulate activity on the nerve.

In embodiments, the pulses in a set of pulses can be monophasic or biphasic or a mixture of monophasic and biphasic, or some other complex waveform.

In embodiments, the set of pulses at the first selected frequency can be delivered once or more than once during the on time. If a set of pulses is delivered more than once during the on time, the set of pulses are referred to as a burst of signal. In embodiments, there may be a delay period between the sets of pulses. The delay period between each burst may be the same or different. In an embodiment, more than one burst of pulses having a frequency of at least 150 Hz are delivered during an on time. Each burst lasts at least about 26 milliseconds, and each burst is separated by a delay period of at least about 0.3 seconds.

In embodiments, the therapy cycle is a low charge therapy cycle delivering a total charge of 0.2 coulombs or less to the nerve. In embodiments, the total amount of charged delivered in a therapy cycle is about 5 microcoulombs to about 100,000 microcoulombs, more preferably about 10 microcoulombs to about 50,000 microcoulombs, more preferably about 10 microcoulombs to about 10,000 microcoulombs, or more preferably about 10 microcoulombs to about 1000 microcoulombs. In embodiments, the therapy cycle comprising at least one set of pulses having a frequency of at least 150 Hz delivers about 5 microcoulombs of charge or greater. While not meant to limit the scope of the disclosure, it is believed that a low charge therapy cycle as described herein provides for at least partial downregulation of nerve activity while conserving the energy required to power the therapy cycle. In embodiments, the amount of required energy is decreased so that a primary battery rather than a rechargeable battery may be employed in the systems described herein.

In embodiments, the electrical signal that further comprises: a) a set of pulses applied at a second selected frequency of about 1-10,000 Hz, wherein each pulse of the set of pulses has a pulse width of at least 0.05 microseconds and less than the period of the selected frequency. In embodiments, the second selected frequency is different than the first selected frequency.

The second selected frequency can range from about 1 to about 10,000 Hz. In other embodiments, the first selected frequency has a frequency of about 1 to 1000 Hz, preferably about 1 to 200 Hz, preferably about 1 to 150 Hz, preferably about 1 to 50 Hz, or preferably about 1 to 10 Hz. In an embodiment, the second selected frequency is about 40 Hz or greater, and has a pulse width of about 0.05 microseconds or greater.

In embodiments, the pulse or set of pulses have a current amplitude of about 0.1 to 20 mAmps, preferably about 0.1 to 15 mAmps, preferably about 0.1 to 10 mAmps, preferably about 0.1 to 5 mAmps, preferably about 0.1 to 1 mAmp, preferably about 6 to 20 mAmps, preferably about 10 to 20 mAmps, or preferably about 10 to 16 mAmps.

In embodiments, the pulse width of each pulse is about 0.05 microseconds to about 0.5 second, preferably about 0.1 microseconds to about 0.1 seconds, preferably about 0.5 microseconds to about 0.05 seconds, or preferably about 1 microsecond to 0.006 seconds.

In embodiments, the pulses in a set of pulses can be monophasic or biphasic or a mixture of monophasic and biphasic, or some other complex waveform.

In embodiments, the set of pulses at the second selected frequency can be delivered once or more than once during the on time. If a set of pulses is delivered more than once during the on time, the set of pulses are referred to as a burst of signal.

In embodiments, there may be a delay period between the sets of pulses. The delay period between each burst may be the same or different. In an embodiment, more than one burst of pulses having a frequency of at less than 150 Hz are delivered during an on time. In embodiments, each burst has about 1 to about 20 pulses, and lasts at least about 10 microseconds, and each burst is separated by a delay period of at least 2.5 milliseconds.

In embodiments, the therapy cycle is a low charge therapy cycle delivering a total charge of 0.2 coulombs or less to the nerve. In embodiments, the total amount of charged delivered in a therapy cycle is about 5 microcoulombs to about 100,000 microcoulombs, more preferably about 10 microcoulombs to about 50,000 microcoulombs, more preferably about 10 microcoulombs to about 10,000 microcoulombs, or more preferably about 10 microcoulombs to about 1000 microcoulombs. In embodiments, the therapy cycle comprising at least one set of pulses having a frequency of less than 150 Hz delivers about 5 microcoulombs of charge or greater.

In embodiments, the set of pulses applied at a first selected frequency of 150 Hz or greater is followed by the set of pulses applied at a second selected frequency of about 1-10,000 Hz. In other embodiments, the set of pulses applied at a second selected frequency of about 1-10,000 Hz is followed by the set of pulses applied at a first selected frequency of 150 Hz or greater. In yet other embodiments, one or more of the set of pulses may be applied simultaneously or overlapping one another.

In embodiments, an on time of the therapy cycle is at least 30 seconds, more preferably about 30 seconds to 30 minutes, 30 seconds to 20 minutes, 30 seconds to 10 minutes, 30 seconds to 5 minutes, 30 seconds to 2 minutes, and 30 seconds to 1 minute. In embodiments, the therapy cycle has an offtime during which no signal is delivered. In embodiments, the time of the off time is selected to allow at least partial recovery of nerve activity. In embodiments the offtime is at least 30 seconds, more preferably 30 seconds to 30 minutes, 30 seconds to 20 minutes, 30 seconds to 10 minutes, 30 seconds to 5 minutes, 30 seconds to 2 minutes, and 30 seconds to 1 minute. A therapy cycle can comprises one or more on times and one or more offtimes. In an embodiment, the therapy cycle includes 2 minutes of on time, 1 minute of off time, 2 minutes of on time, and 5 minutes of off time. While not meant to limit the scope of the inventive subject matter, it is believed that electrical signals that are delivered with an on time and an off time minimize gastric accommodation, decrease discomfort for the patient, and minimize damage to the nerve.

In embodiments, the neuroregulator is configured to deliver one or more than one therapy cycle in a treatment period. A treatment period ranges from about 6 to 24 hours, preferably 6 to 18 hours, 6 to 12 hours, and 6 to 9 hours. In an embodiment, a treatment period is at least 6 hours.

In embodiments, the therapy cycle comprises an electrical signal comprising: a) a set of pulses that have a frequency of about 150 Hz or greater; and b) a total amount of charge delivered to the nerve of about 5 microcoulombs to about 200,000 microcoulombs during the therapy cycle. While not meant to limit the scope of the invention, it is believed that delivering a low amount of charge during a therapy cycle provides effective treatment while saving energy. In embodiments, the electrical signal is applied at a frequency that at least partially downregulates activity on the nerve.

The total amount of charge delivered during the on time of the therapy cycle can be determined based on the pulse width, current amplitude, frequency and total on time of the signal and are related by the following equation:

Total charge per cycle=(current amplitude)×(pulse width)×(frequency)×(cycle time) (for biphasic pulses, the total charge is reduced by a factor of 2)

In embodiments, the total amount of charged delivered in a therapy cycle is about 10 microcoulombs to about 100,000 microcoulombs, more preferably about 10 microcoulombs to about 50,000 microcoulombs, more preferably about 10 microcoulombs to about 10,000 microcoulombs, or more preferably about 10 microcoulombs to about 1000 microcoulombs.

In some embodiments, a therapy cycle further comprises one or more electrical signals having a second selected frequency of less than 150 Hz, and an on time of at least 30 seconds. In embodiments, the frequency of about 150 Hz or greater is different than the second selected frequency. During the on time both the frequency of about 150 Hz or greater and the second selected frequency signals are delivered to the nerve. In embodiments, the signal having a frequency of about 150 Hz or greater is referred to as a high frequency signal and the second selected frequency signal is referred to as a low frequency signal.

In some embodiments, the frequency of about 150 Hz or greater of the electrical signal ranges from about 150 to 10,000 Hz, about 200 to 8000 Hz, or about 500 to 5000 Hz. In some embodiments, the frequency of about 150 Hz or greater of the electrical signal is about 500 to 1000 Hz. In embodiments, a signal having a frequency of about 150 Hz or greater comprises a frequency of 200 Hz or greater and include a plurality of charge pulses with pulse widths of about 0.06 to 3000 milliseconds, about 25 to 300 milliseconds, or about 0.06 to 100 milliseconds. In embodiments, a signal having a frequency of about 150 Hz or greater can comprise a frequency of 200 Hz or greater, and have a current amplitude of about 1 to 20 mAmp, about 1 to 6 mAmp, or about 1 to 3 mAmp. In embodiments, a signal having a frequency of about 150 Hz or greater comprises a frequency of 200 Hz or greater, pulse widths of 60 microseconds or greater.

In some embodiments, one or more second selected frequency electrical signal is about 0.5 to 199 Hz, 1 to 150 Hz, or 10 to 100 Hz. In some embodiments, the second selected frequency of the electrical signal is about 10 to 50 Hz. In embodiments, a second selected frequency electrical signal can include a plurality of charge pulses with pulse widths of about 0.025 to 25 microseconds or about 0.05 to about 0.5 microseconds. In embodiments, the low frequency signal comprises packets of 1 to 20 pulses, each pulse having a pulse width of 500 nanoseconds or less. In embodiments, a second selected frequency signal has a frequency of less than 200 Hz and has a current amplitude of 1 mAmp or less. In embodiments, a second selected frequency signal comprises a frequency of less than 200 Hz, and a pulse width of about 100 to 500 nanoseconds. In embodiments, a third selected frequency signal comprises a frequency of less than 200 Hz, and a pulse width of 50 to 500 nanoseconds.

In embodiments, the voltage of each signal can vary. In embodiments of the signal having a frequency of about 150 Hz or greater, the voltage is about 1 to 24 volts. In embodiments, the second selected frequency signal has a voltage of about 1 to 15 volts, or 5 to 15 volts. In embodiments, the second selected frequency signal has a voltage of about 0.1 to about 2 volts, or 0.2 volts to 1 volt.

In some embodiments, additional signals at the low frequency will be numbered numerically, e.g., third selected signal, fourth selected signal, etc. While not meant to limit the scope of the disclosure, it is believed that the combination of the high frequency signal and a low frequency signal provides at least a partial downregulation of activity on the nerve.

In embodiments, a therapy cycle comprises one or more additional selected frequency electrical signals that are delivered simultaneously, precede, follow, or precede and follow a signal having a frequency of about 150 Hz or greater. In embodiments, a second selected frequency signal, a third selected frequency signal, and a signal having a frequency of about 150 Hz or greater can be delivered simultaneously during an on time of the therapy cycle, each signal having at least one parameter that differs from the other signals. In embodiments, the second selected frequency signal can be applied first followed by the signal having a frequency of about 150 Hz or greater followed by the third selected frequency signal during an on time. In an embodiment, the second and third selected frequency signals are initiated and applied throughout the on time and a signal having a frequency of about 150 Hz or greater is delivered after the initiation of the second and third selected frequency signals. In an embodiment, a third selected frequency signal can be applied first and overlap with a signal having a frequency of about 150 Hz or greater, and then the second selected frequency signal continues in concert with the third selected frequency signal during the on time. In an embodiment, a second selected frequency signal can be applied first and overlap with a signal having a frequency of about 150 Hz or greater, and then the third selected frequency signal is applied during the on time. In embodiments, the second and third selected frequency signals are applied throughout the on time and the high frequency signal is delivered once during the on time.

In embodiments, an on time for therapy cycle can range from 1 second to 30 minutes or more, 30 seconds to 5 minutes, from 30 seconds to 10 minutes, or from 1 second to 2 minutes. The on time can optionally include a ramp up and a ramp down time of about 2 to 60 seconds. The off times of the electrical signal in the therapy cycle are selected to allow for at least partial recovery of nerve activity. In embodiments, the off times can be selected from about 30 seconds to about 20 minutes, 1 minute to 10 minutes, or 1 minute to 5 minutes.

The implantable component may be configured to generate therapy cycles for a treatment period. The therapy cycles can be continuous or intermittent. In some cases, the treatment period is at least 6 hours. In embodiments, a treatment period is from 30 minutes to 24 hours, 30 minutes to about 12 hours, 30 minutes to 9 hours, 30 minutes to 8 hours, or 30 minutes to 6 hours. In embodiments, a therapy cycle comprises 30 minutes of continuous electrical signal treatment on time with no off times. In embodiments, the external programmer is configured to provide therapy instructions that include multiple therapy cycles per treatment period. The external programmer may also provide for one or more than one treatment periods per day or per week. In some embodiments, treatment periods may be related to the period of time before and after eating of a meal.

Normally a patient would only use the device while awake. The hours of therapy delivery can be programmed into the device by the clinician (e.g., automatically turns on at 7:00 AM and automatically turns off at 9:00 PM). In the RF-powered version of the neuroregulator, use of the device is subject to patient control. For example, a patient may elect to not wear the external antenna. The device keeps track of usage by noting times when the receiving antenna is coupled to the external antenna through radio-frequency (RF) coupling through the patient's skin.

The flexibility to vary average vagal activity gives an attending physician great latitude in treating a patient. For example, in treating obesity, the electrical signal can be applied with a short "off" time to reduce weight as rapidly as possible. The parameters may be varied in accord with the weight loss occurring over time. The system provides data with regard to actual patient use and therapy delivery time and such data can be used to modify the parameters of the therapy cycle. For example, the number of therapy cycles may be initially much higher when the patient has more weight to lose and may be adjusted downward to a maintenance mode once the weight loss goal is achieved. The therapy may be discontinued for a period of time if the patient continues to lose weight beyond the goal weight loss.

If the patient experiences discomfort due to dysmotility, the duration of the "off" period can be increased to improve patient comfort. Also, the reduction of enzyme production can result in decreased fat absorption with consequential increase of fat in feces. The on and off duration can be adjusted to achieve tolerable stool (e.g., avoiding excessive fatty diarrhea). The control afforded by the present invention can be used to prevent the enteric nervous system's assumption of control since vagal activity is not completely interrupted as in the case of a surgical and permanent vagotomy.

While patient weight loss and comfort may be adequate, as feedback for determining the proper parameters for duration of on time and off time, more objective tests can be developed. For example, the duration of on time and off time can be adjusted to achieve desired levels of enzyme production and nutrient digestion. In one example of drug therapy for obesity, orlistat blocks the action of lipase. Lipase is a fat-digesting enzyme. As a consequence of this reduction in lipase, the fat content of feces increases. It is generally regarded as desirable to modulate drug intake so that fecal fat does not exceed 30% of ingested fat. Similarly, the on and off time durations can be modulated to achieve the same result. Such testing can be measured and applied on a per patient basis or performed on a statistical sampling of patients and applied to the general population of patients.

In embodiments, the parameters of the therapy cycle can be selected based on the starting blood pressure of the subject, such as a systolic blood pressure of at least 140 mmHg or a diastolic blood pressure of 90 mmHg. In embodiments, if the amount of change in systolic blood pressure is less than 5 mmHg, parameters and/or therapy cycles are adjusted to decrease blood pressure at least 10 mmHg. Parameters and/or therapy cycles may be adjusted once or more than once in order to reach a systolic blood pressure of at least 130 mmHg.

In another embodiment, the parameters of the therapy cycle are selected based on the Patients with Type 2 diabetes have a fasting plasma glucose of 126 mg/dl or greater; oral glucose tolerance of 200 mg/dl or greater; and/or % of HbA1C of 6.5% or greater. In some cases, the HbA1C percentage is 6-7%, 7-8%, 8-9%, 9-10%, and greater than 10%. In embodiments, if the amount of change in % of HbA1C is less than 0.5% parameters and/or therapy cycles are adjusted to decrease % of HbA1C at least 1%. Parameters and/or therapy cycles may be adjusted once or more than once in order to reach a % of HbA1C of at least 7%.

In some embodiments, a sensing electrode SE is added to the system to monitor vagal activity as a way to determine how to modulate the on and off time durations. While a sensing electrode can be an additional electrode, it will be appreciated a single electrode could perform both functions. The sensing and therapy electrodes can be connected to a neuroregulator as shown in FIG. 3. When the sensing electrode SE yields a signal representing a targeted maximum vagal activity or tone (e.g., 50% of baseline) the neuroregulator with the additive function of receiving a signal from the sensing electrode energizes the electrode with a signal. As described with reference to neuroregulator 104, neuroregulator with the additive function of receiving a signal from the sensing electrode can be remotely programmed as to parameters of on duration and off duration as well as targets for initiating a therapy cycle.

The apparatus and method described herein use recovery of the vagus nerve to control a degree of down-regulation of vagal activity. This gives a physician enhanced abilities to control a patient's therapy for maximum therapeutic effectiveness with minimum patient discomfort. Therefore, the vagal modulation of the present invention can be used as treatment for other conditions associated with excess weight.

3) Methods in Combination

The disclosure provides methods for treating a condition associated with excess weight that include administering to a subject a composition comprising an agent that affects weight loss, blood pressure, and/or blood sugar.

In some embodiments, the agent will increase energy expended and/or decrease the amount of energy consumed. Agents that affect weight loss are known to have certain characteristics, for example, some agents enhance the sensation of satiety, other agents decrease appetite (anorexic), others block the absorption of fat or other nutrients, others inhibit enzymes that digest fat, some agents are thermogenic, and some have combinations of effects.

Agents that affect weight loss can be selected based on an ability to complement treatment of applying a signal to downregulate neural activity of the vagal nerve. Drugs that have been approved by the FDA to treat obesity include sibutramine and orlistat for long term use; and phentermine for short tem' use. However, the excess weight loss associated with administration of these drugs is limited to a maximum of about 10% when compared with loss due to diet and exercise alone. As described herein, an agent is selected that may provide a complementary or synergistic effect with the application of signal to modulate neural activity on the vagus nerve. A synergistic or complementary effect can be determined by determining whether the patient has an increase in excess weight loss as compared to one or both treatments alone. In some embodiments, agents that act at a different site (e.g. hypothalamus or pituitary) or through a different pathway may be selected for use in the methods described herein. Agents that complement treatment are those that include a different mechanism of action for affecting the excess weight of the subject.

An agent may also or in addition be selected to administer that may have undesirable side effects at the recommended dosage that prevents use of the agent, or that prevents compliance by the patient. In addition, patients that have excess weight as well as hypertension, cardiac conditions, liver disease, or renal disease may not be able to tolerate treatment with one or more of the agents at the recommended dosage due to adverse side effects. Agents that have undesirable side effects include fenfluramine, and dexfenfluramine which have been shown to have adverse effects on blood pressure and to be associated with valvular heart disease. Other drugs such as bupropion can cause seizures. Drugs that inhibit fat absorption, such as orlistat, can cause diarrhea, soft and oily stools, and flatulence. Other drugs may cause central nervous system symptoms such as anxiety, cognitive deficits, depression, and/or nervousness.

Combining administration of a drug with undesirable side effects with modulating neural activity on the vagus nerve may allow for administration of the drugs at a lower dose thereby minimizing the side effects. In addition, a drug may be selected that has altered pharmacokinetics when absorption is slowed by a delay in gastric emptying due to neural downregulation as described herein. In other embodiments, the recommended dosage may be lowered to an amount that has fewer adverse side effects. In some embodiments, the therapeutic window may be increased. In some embodiments, a drug that may be useful for short term use may be administered for long term use at the lowered dosage. For example, a drug such as rimonabant at 20 mg per dose may be lowered to a 5 mg dose and still be effective for weight loss. In embodiments, it is expected that the recommended dosage may be able to be lowered at least 25%. In other embodiments, the dosage can be lowered to any percentage of at least 25% or greater of the recommended dose. In some embodiments, the dosage is lowered at least 25, 30, 35, 40, 45, 50, 55, 60, 65, 70, 75, 80, 85, 90, 95, or 100% of the recommended dosage.

Agents that affect the hypothalamic or neuroendocrine function such as ghrelin, ghrelin agonists, ghrelin antagonists, leptin agonist, leptin antagonists, ciliary neurotrophic factor (CNTF), CNTF analogues, amylin, and amylin analogues may complement effects on the vagus nerve. In addition, agents that enhance the sensation of satiety and reduce appetite and act on neurotransmitters in the brain may complement the effects of neural downregulation on the vagus nerve. Such agents include neurotransmitter releasers, inhibitors of the uptake of serotonin, norepinephrin, and dopamine. These agents include, for example, sibutramine, fenfluramine, phentermine, dexphenfluoramine, flouxetine, and bupropion. Agents that are thermogenic increase energy expenditure of the patient and would have a complementary effect to that of modulating the neural activity of the vagus nerve. These agents include, for example, sibutramine, leptin, leptin agonists, leptin analogues, CNTF, and CNTF analogues. Agents that suppress appetite and enhance the feeling of satiety include incretins including GLP-1, PYY, CKK, and oxyntomodulin.

In the methods of the disclosure, an anorexic agent may be administered. Several anorexic agents are known to those of skill in the art. Anorexic agents include phentermine, fenfluramine, dexfenfluramine, endocannabinoid receptor antagonists, ghrelin antagonists, orexin antagonists, somatostatin receptor agonist, GLP-1, PYY, and cholecystokinin agonists. Endocannaboid receptor antagonists are known and include rimonabant. Phentermine has been approved for short term treatment of obesity.

Thermogenic agents are attractive as they increase the energy expenditure of the subject. Leptin, for example, may reduce calorie intake and increases energy expenditure through action on the sympathetic nerve system. Other agents that have thermogenic characteristics include sibutramine, leptin, leptin agonist, a leptin analogue, ciliary neurotrophic factor (CNTF), and a CNTF analogue. Axokine is a CNTF analogue that has been shown to promote weight loss. Sibutramine has been approved for long term treatment of obesity.

Agents that inhibit fat absorption are more likely to have effects similar to that of modulating neural activity of the vagus nerve rather than complementary effects. Even though the action of agents that inhibit fat absorption may not be complementary to downregulation of vagal nerve activity, they have undesirable side effects that may contribute to a lack of patient compliance. Such side effects include diarrhea, flatulence and loose stools. Some agents inhibit the action of lipases that break down fat in ingested food. Agents that inhibit fat absorption include orlistat or a lipin inhibitor. Orlistat has been approved for long term treatment of obesity.

Agents that enhance satiety through a CNS pathway, such as a hypothalamic or neuroendocrine pathway, would have effects complementary to those due to treatment by modulating neural activity on the vagus nerve. Agents that enhance satiety include somatostatin receptor agonists, GLP-1 agonists, GLP-1 variants, peptide PYY, POMC agonists, neuropeptide Y inhibitors, topiramate, tegretol, bupropion, naltrexone, zonisamide, amylin, amylin analogues, and oxyntomodulin. Pramlitidine is an amylin analogue that has shown effectiveness in clinical trials for weight loss. Exendin-4 is a potent and long lasting GLP-1 analogue and agonist of GLP-1. Liraglutide is also a long acting analogue of GLP-1. Administration of PYY increases propiomelanocortin activity and has been shown to result in decreased food consumption. Oxyntomodulin suppresses appetite and food intake.

Sequences for the polypeptides such as GLP-1, ghrelin, leptin are known to those of skill in the art and are described in publicly available databases. Representative sequences are: Leptin (gI 1469860 and gI4557715); ghrelin (gI 37183224); POMC (GI 190188); GLP-1(gI 125987831 (P01275)); CKKB receptor (gI 417029); CNTF (gI 633830, gI 825643, gI116585); PYY (gI 71361686, gI 1172776); orexin (gI 4557635); somatostatin receptor (gI 431095, gI 307430) and amylin (gI 457131, gI 4557655).

In some embodiments, the patient has a condition associated with excess weight including obesity, compulsive eating, and/or bulimia. In some embodiments, a patient may be selected that is not yet obese but is overweight. Excess weight of at least 10 pounds or 10-20 pounds is associated with adverse health effects. Overweight and obesity classifications include those determined by body mass index (BMI) (calculated as weight in kilograms divided by the square of height in meters). For example, normal weight: BMI=18.5-24.9; overweight: BMI=25.0-29.9; obesity-class 1: BMI=30.0-34.9; obesity-class 2: BMI=35.0-39.9; obesity-class 3: BMI>40.0). Of course these ranges may vary given the height, gender, and age of the subject. In other embodiments, the patient at least has a body mass index (BMI) of at least 25 or greater. In other embodiments, the patient has a BMI of at least 27 to about 30 and also has other health conditions such as hypertension, diabetes, cardiovascular disease, liver disease, and/or renal disease. In other embodiments, the patient is overweight at least 10 pounds and/or has a condition such as type II diabetes, asthma, arthritis, hypertension, high cholesterol, and/or cardiovascular disease.

The disclosure provides methods for treating a condition associated with impaired glucose regulation that include neuroregulation as well as administering to a subject a composition comprising an agent that affects glucose control in a subject. In some embodiments, the agent increases the amount of insulin present in the blood. In other embodiments, the agent increases insulin sensitivity. In some embodiments, the agent reduces endogenous glucose production and/or glucose absorption.

Several pathways are known to affect energy balance. Pathways include gut-hypothalamic axis (e.g. ghrelin), gut-hindbrain axis (e.g. vagus nerve), peripheral tissue (adipose tissue, skeletal muscle)-hypothalamic axis (e.g. leptin), and hypothalamic-hindbrain axis (neural projections). In particular, the hypothalamus (forebrain) and the area postrema (hindbrain) are 2 regions of the central nervous system which are thought to play orchestrating roles in the human energy homeostasis. It has been documented that there are neural connections between these two regions enabling communications and complementary, as well as, redundant effects on body energy balance. Numerous hormones, enzymes, neurotransmitters, and other mediators are released from different parts of these pathways and can have influences on these regions of the central nervous system. Utilization of distinct treatment modalities that involve different parts of these pathways and brain regions, thus altering the communication between the central nervous system and gut, pancreas, liver, muscle, and fat cells may be of importance in combinatorial therapy that is highly effective, robust, and durable.

Agents that affect impaired glucose control can be selected based on an ability to complement treatment of applying a signal to alter neural activity of a target nerve. As described herein, an agent is selected that may provide a complementary or synergistic effect with the application of signal to modulate neural activity on a target nerve such as the vagus nerve. A synergistic or complementary effect can be determined by determining whether the patient has an improvement in glycemic control as described herein as compared to one or both treatments alone.

In some embodiments, agents that act at a different site (e.g. hypothalamus or pituitary) or through a different pathway may be selected for use in the methods described herein. Agents that complement treatment are those that include a different mechanism of action for affecting the glycemic control of the subject. In some embodiments, a synergistic effect may be observed with an agent that does not affect glucose digestion and/or delay gastric emptying, such as an agent that increases insulin secretion, insulin sensitivity, and/or decreases endogenous glucose production. Such agents include insulin, amylin analogues, insulin secretagogues, sulfonylureas, meglitinides and PPAR alpha, gamma and delta agonists.

An agent may also or in addition be selected to be administered that may have undesirable side effects at the recommended dosage that prevents use of the agent, or that provides inadequate glycemic control. In addition, patients that have hypertension, cardiac conditions, liver disease, or renal disease may not be able to tolerate treatment with one or more of the agents at the recommended dosage due to adverse side effects.

Agents that have undesirable side effects include Avandia (rosiglitazone; PPAR-gamma agonist) which has been shown to have adverse effects on cardiovascular conditions and cause weight gain. Drugs that inhibit or slow gastric emptying, such as amylin analogs or GLP-1 analogs, or drugs that are irritants to the GI track, such as metformin (biguinide) can cause nausea, vomiting, and diarrhea. Drugs that alter breakdown and absorption of carbohydrate in the GI track, such as Precose (acarbose; alpha-glucosidase inhibitor) can cause diarrhea and flatulence. Drugs that increase blood insulin concentrations, such as exogenous insulin administration, sulfonylureas, and meglitinides can cause hypoglycemia and weight gain.

The disclosure provides methods for treating a condition associated with impaired blood pressure and/or heart rate that include administering to a subject a composition comprising an agent that affects blood pressure and/or heart rate in a subject. In some embodiments, the patients may be refractory to one or more pharmaceuticals for treatment of elevated blood pressure. In that case, modulation of vagal nerve activity may be employed without administration of other agents. In other cases, for patients refractory to one or more drugs a combination of modulation of vagal nerve activity with administration of one or more agents may be beneficial. In other embodiments, a drug used to treat a cardiac condition may be associated with hypotensive effects and therefore the drug may be administered with an electrical treatment signal that increases blood pressure.

Agents that affect impaired blood pressure control can be selected based on an ability to complement treatment of applying a signal to alter neural activity of a target nerve. As described herein, an agent is selected that may provide a complementary or synergistic effect with the application of signal to modulate neural activity on a target nerve such as the vagus nerve. A synergistic or complementary effect can be determined by determining whether the patient has an improvement in blood pressure and/or heart rate as described herein as compared to one or both treatments alone.

In some embodiments, agents that act at a different site or through a different pathway may be selected for use in the methods described herein. Agents that complement treatment are those that include a different mechanism of action for affecting the heart rate and/or blood pressure control of the subject.

An agent may also or in addition be selected to be administered that may have undesirable side effects at the recommended dosage that prevents use of the agent, or that provides inadequate blood pressure control. In addition, patients that have cardiac conditions, liver disease, or renal disease may not be able to tolerate treatment with one or more of the agents at the recommended dosage due to adverse side effects.

Combining administration of a drug with undesirable side effects with modulating neural activity on a target nerve may allow for administration of the drugs at a lower dose thereby minimizing the side effects, may allow for administration of a single drug instead of multiple drugs, or may allow administration of higher doses of the drugs. In addition, a drug may be selected that has altered pharmacokinetics when absorption is slowed by a delay in gastric emptying due to neural downregulation as described herein. In other embodiments, the recommended dosage may be lowered to an amount that has fewer adverse side effects. In embodiments, it is expected that the recommended dosage may be able to be lowered at least 25%. In other embodiments, the dosage can be lowered to any percentage of at least 25% or greater of the recommended dose. In some embodiments, the dosage is lowered at least 25, 30, 35, 40, 45, 50, 55, 60, 65, 70, 75, 80, 85, 90, 95, or 100% of the recommended dosage.

In an embodiment, a method provides a treatment for a condition associated with impaired blood pressure and/or heart rate. Conditions associated with impaired blood pressure and/or heart rate include, hypertension, prehypertension, congestive heart failure, ischemic heart disease, coronary artery disease, chronic renal disease, and cerebral vascular disease. A method comprises selecting a drug useful for treating hypertension or congestive heart failure and having a recommended dosage for efficacy where a patient is likely to experience disagreeable side effects at said recommended dosage; and treating the patient with a concurrent treatment comprising: applying an intermittent neural block to a target nerve of the patient at multiple times per day and over multiple days with the block selected to down-regulate afferent and/or efferent neural activity on the nerve and with neural activity restoring upon discontinuance of said block; and administering said drug to the patient at a dosage less than said recommended dosage. In some embodiments, the effective dosages for such a patient are associated with disagreeable side effects contributing to said patient not complying with a drug treatment. In some embodiments, patients are those that have cardiac conditions, liver, or renal disorder and may not be able to tolerate treatment with one or more of the agents.

A method comprises selecting a drug useful for treating a cardiac condition and having a recommended dosage for efficacy where a patient is likely to experience disagreeable side effects at said recommended dosage such as hypotension; and treating the patient with a concurrent treatment comprising: applying an intermittent neural conduction signal to a target nerve of the patient at multiple times per day and over multiple days with the signal selected to up-regulate neural activity and with neural activity restoring upon discontinuance of said signal; and administering said drug to the patient at a dosage less than said recommended dosage. In embodiments, the target nerve is the vagus nerve at a location below vagal innervation of the heart.

A number of oral and parenteral medications are available for the treatment of hypertension. Some of these medications are also commonly employed for the treatment of congestive heart failure.

Beta-blockers (beta-adrenergic blockers) work by reducing sympathetic nerve input to the heart. Thus, the heart beats less often per minute and with less force. Subsequently, the heart reduces its work, and blood pressure drops. Beta-blockers include propranolol, metoprolol, atenolol, and many others. Alpha-blockers (alpha-adrenergic blockers) target the nervous system to relax blood vessels, allowing blood to pass more easily. Examples of alpha blockers are doxazosin, prazosin, and terazosin. Alpha-beta-blockers (alpha- and beta-adrenergic blockers) basically have the same effect as a combined alpha-blocker and beta-blocker. They target the nervous system to relax the blood vessels, as well as work to slow the heartbeat. As a result, less blood is pumped through wider vessels, decreasing the overall blood pressure. Alpha-beta-blockers include labetalol and carvedilol.

Diuretics cause the body to excrete water and salt. This leads to a reduction in plasma volume, which subsequently lowers systemic blood pressure. Diuretics include furosemide, hydrochlorothiazide, and spironolactone.

Angiotensin Converting Enzyme (ACE) inhibitors work by preventing the body's production of angiotensin II, a hormone that normally causes blood vessels to narrow. Consequently, the vessels remain wider, which lowers blood pressure. Angiotensin II also normally stimulates the release of another hormone, called aldosterone, which is responsible for the body's retention of sodium. Hence, in addition to creating wider vessels, ACE inhibitors mimic the effect of diuretics to a certain extent. As a result, blood vessels are subject to less pressure, and the heart performs less work. Examples of ACE inhibitors include enalapril, captopril, and lisinopril. Angiotensin II antagonists are primarily used for patients who develop a cough as a side effect of taking ACE inhibitors. This medication antagonizes angiotensin II, thus inhibiting its effects. Examples include losartan and valsartan.

Calcium channel blockers keep calcium from entering the muscle cells of the heart and blood vessels. The heart and vessels relax, allowing blood pressure to go down. Some calcium channel blockers are nifedipine, verapamil, and diltiazem.

Vasodilators work by relaxing the muscle in the blood vessel wall. Hydralazine and minoxidil are both generic forms of vasodilators.

Dosages for administration to a subject can readily be determined by one of skill in the art. Guidance on the dosages can be found, for example, by reference to other drugs in a similar class of drugs. For example, dosages have been established for any of the approved drugs or drugs in clinical trials and the range of dose will depend on the type of drug. For example, pramlintide dosages range from about 240 micrograms up to 720 micrograms per day. A dosage of sibutramine of 5 to 20 mg per day is recommended.

Dosages associated with adverse side effects are known or can also be readily determined based on model studies. For example, dosages of 30 mg per day or greater of fenfluramine in combination with dexphenfluramine were associated with valvular heart conditions. Risk of seizures and increase in blood pressure with bupropion treatment increases at doses of 300 mg per day or greater. A determination of the effective doses to achieve excess weight loss while minimizing side effects can be determined by animal studies.

The agents or drugs will be formulated, dosed, and administered in a fashion consistent with good medical practice. Factors for consideration in this context include the particular disorder being treated, the particular mammal being treated, the clinical condition of the individual patient, the age of the patient, other medications that the patient is taking, the cause of the disorder, the site of delivery of the agent, the method of administration, the scheduling of administration, and other factors known to medical practitioners. The agent need not be, but is optionally formulated with one or more agents currently used to prevent or treat the disorder in question. The effective amount of such other agents depends on the amount of agent that alters an energy balance of the subject present in the formulation, the type of disorder or treatment, and other factors discussed above. These are generally used in the same dosages and with administration routes as used hereinbefore or about from 1 to 99% of the heretofore employed dosages.

The agents or drugs can be administered at the same time that the subject is receiving a therapy signal treatment, after therapy signal treatment has been administered and is ongoing, when therapy signal treatment is providing for maintenance of weight loss. For example, the implantable device can be implanted and the subject undergoes therapy for a period of at least 1 month to determine the rate of excess weight loss using the device. The rate and amount of excess weight loss using the implantable device can be determined and if weight loss is not adequate (e.g., less than 1% excess weight loss) then the therapy cycle parameters may be adjusted and/or an agent that affects weight loss can be administered. In most cases, the implantable device will deliver therapy for a period of time before the agent is administered to the subject. An agent that affects weight loss may be administered in those patients that appear to be low responders or intermediate responders to the electrical signal treatment.

Therapeutic formulations comprising the agent are prepared for storage by mixing the agent having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated. In certain such embodiments, the compounds have complementary activities that do not adversely affect each other. Such molecules are suitably present in combination in amounts that are effective for the purpose intended.

The therapeutic agent is/are administered by any suitable means, including parenteral, subcutaneous, orally, intradermal, intraperitoneal, and by aerosol. Parenteral infusions include intramuscular, intravenous, intraarterial, intraperitoneal, or subcutaneous administration. Pumps may be utilized as well as drug eluting devices and capsules.

Modifications and equivalents of disclosed concepts such as those which might readily occur to one skilled in the art are intended to be included in the scope of the claims which are appended hereto. For example, while the foregoing example is described with reference to applying signals to vagus nerves to treat obesity, the invention is applicable to other conditions associated with excess weight amenable to treatment by down-regulating or otherwise modulating activity of the vagus nerve.

In the sections of this application pertaining to teachings of the prior art, the specification from prior art patents is substantially reproduced for ease of understanding the embodiment of the present invention. For the purpose of the present application, the accuracy of information in those patents is accepted without independent verification. Any publications referred to herein are hereby incorporated by reference.

What is claimed is:

1. A system for treating a gastrointestinal disorder or a condition associated with excess weight in a subject in need thereof comprising:
    at least one electrode adapted to be placed at a vagus nerve;
        an implantable neuroregulator configured to apply a therapy cycle to the electrode, wherein each therapy cycle comprises a) a high frequency burst of electrical signal having a first selected frequency of at least 1000 Hz, wherein the high frequency burst of electrical signals comprises one or more pulses that have a pulse width of about 0.01 milliseconds to about 0.09 milliseconds, and a current of about 0.1 to 20 mAmps; b)more than one burst having a low frequency, each burst having a second selected low frequency of at least 40 Hz and less than 150 Hz, wherein each of the bursts of low frequency electrical signals comprises one or more pulses that have a pulse width of about 0.05 microseconds to about 0.5 microseconds, a current of about 0.1 to 20 mAmps and a delay period between each burst; wherein the high frequency and low frequency are delivered during the same therapy cycle and at least partially downregulate activity on the nerve; c) an on period of at least 2 minutes d) an off period, wherein the off period is selected to allow at least partial recovery of nerve activity; and e) a total charge of about 5 to 1000 microcoulombs or less per therapy cycle.

2. The system according to claim 1, wherein a first burst of low frequency signal precedes the high frequency signal and a second burst of low frequency signal follows the high frequency signal.

3. The system according to claim 1, wherein the gastrointestinal disorder or condition is selected from the group consisting of obesity, hypertension, diabetes, and combinations thereof.

4. The system of claim 1, wherein the first selected frequency is selected from about 1000 to 5000 Hz.

5. The system of claim 1, wherein the one or more set of pulses has about 1-20 pulses.

6. The system of claim 1, wherein the low frequency electrical signal has a current amplitude of about 1 mAmp or less.

7. The system of claim 1, wherein the implantable neuro-regulator is further configured to apply one or more therapy cycles in a treatment period.

8. The method of claim 7, wherein the treatment period is at least 6 hours.

9. A method of selecting parameters for a therapy cycle for an implantable device in a subject comprising:
   selecting parameters of a therapy cycle to be applied to a vagus nerve, wherein the therapy cycle comprises an electrical signal comprising i)) a set of pulses applied at a first selected frequency of at least 1000 Hz, wherein each pulse of the set of pulses has a pulse width of at least 0.01 milliseconds and less than the period of the first selected frequency; b) communicating the selected parameters to the implantable device comprising the system of claim 1; and c) determining the amount of actual therapy delivered over a time period and adjusting the length of the treatment period to increase the amount of excess weight loss, to affect the blood pressure, and/or diabetes of the subject.

10. The method of claim 9, further comprising selecting the parameters of an electrical signal that comprises: a) a set of pulses applied at a second selected frequency of at least 40 Hz and less than 150 Hz, wherein each pulse of the set of pulses has a pulse width of at least 0.05 microseconds and less than the period of the second selected frequency.

* * * * *